(12) United States Patent
Darmoc et al.

(10) Patent No.: US 9,447,169 B2
(45) Date of Patent: Sep. 20, 2016

(54) FLOWABLE COLLAGEN-BASED HEMOSTAT AND METHODS OF USE

(75) Inventors: Marissa M. Darmoc, Philadelphia, PA (US); Lauren S. Brown, Ardmore, PA (US); Jenny E. Raynor, Phoenixville, PA (US); Alice Chou, Bethlehem, PA (US); Abigail Cohen, Huntington Woods, MI (US)

(73) Assignee: Orthovita, Inc., Malvern, PA (US)

( * ) Notice: Subject to any disclaimer, the term of this patent is extended or adjusted under 35 U.S.C. 154(b) by 0 days.

(21) Appl. No.: 13/411,324

(22) Filed: Mar. 2, 2012

(65) Prior Publication Data

US 2012/0230977 A1 Sep. 13, 2012

Related U.S. Application Data

(60) Provisional application No. 61/449,292, filed on Mar. 4, 2011.

(51) Int. Cl.
*A61K 38/46* (2006.01)
*C07K 14/78* (2006.01)
*A61K 38/39* (2006.01)
*A61K 38/48* (2006.01)

(52) U.S. Cl.
CPC .............. *C07K 14/78* (2013.01); *A61K 38/39* (2013.01); *A61K 38/4833* (2013.01); *C12Y 304/21005* (2013.01)

(58) Field of Classification Search
None
See application file for complete search history.

(56) References Cited

U.S. PATENT DOCUMENTS

| | | | |
|---|---|---|---|
| 4,215,200 A * | 7/1980 | Miyata et al. | 435/273 |
| 4,442,655 A * | 4/1984 | Stroetmann | 53/428 |
| 4,582,640 A * | 4/1986 | Smestad et al. | 530/356 |
| 4,600,574 A | 7/1986 | Lindner et al. | |
| 4,642,117 A | 2/1987 | Nguyen et al. | |
| 4,789,663 A * | 12/1988 | Wallace et al. | 514/16.7 |
| 4,803,075 A | 2/1989 | Wallace et al. | |
| 4,891,359 A * | 1/1990 | Saferstein | A61L 24/0015 424/499 |
| 5,196,185 A | 3/1993 | Silver et al. | |
| 5,204,382 A | 4/1993 | Wallace et al. | |
| 5,352,715 A | 10/1994 | Wallace et al. | |
| 5,428,024 A | 6/1995 | Chu et al. | |
| 5,516,532 A | 5/1996 | Atala et al. | |
| 5,614,587 A | 3/1997 | Rhee et al. | |
| 5,656,492 A * | 8/1997 | Glowacki et al. | 435/284.1 |
| 5,800,372 A * | 9/1998 | Bell et al. | 602/48 |
| 6,020,200 A * | 2/2000 | Enevold | 435/382 |
| 6,063,061 A | 5/2000 | Wallace et al. | |
| 6,066,325 A | 5/2000 | Wallace et al. | |
| 6,162,241 A * | 12/2000 | Coury et al. | 606/214 |
| 6,218,360 B1 * | 4/2001 | Cintron et al. | 514/9.4 |
| 6,280,727 B1 * | 8/2001 | Prior et al. | 424/94.63 |
| 6,454,787 B1 * | 9/2002 | Maddalo et al. | 606/214 |
| 6,706,690 B2 | 3/2004 | Reich et al. | |
| 7,320,962 B2 | 1/2008 | Reich et al. | |
| 2004/0028738 A1 * | 2/2004 | Huang et al. | 424/484 |
| 2004/0110439 A1 * | 6/2004 | Chaikof et al. | 442/123 |
| 2004/0134502 A1 * | 7/2004 | Mizuno et al. | 128/898 |
| 2005/0287215 A1 * | 12/2005 | Looney et al. | 424/485 |
| 2006/0258560 A1 * | 11/2006 | Yang et al. | 514/2 |
| 2006/0286144 A1 * | 12/2006 | Yang et al. | 424/426 |
| 2007/0190101 A1 * | 8/2007 | Yang et al. | 424/423 |
| 2007/0225631 A1 * | 9/2007 | Bowlin et al. | 602/52 |
| 2008/0064839 A1 * | 3/2008 | Hadba et al. | 526/240 |
| 2008/0085316 A1 | 4/2008 | Qian et al. | |
| 2008/0213243 A1 * | 9/2008 | Preiss-Bloom et al. | 424/94.63 |
| 2009/0092674 A1 * | 4/2009 | Ingram et al. | 424/499 |
| 2009/0269413 A1 * | 10/2009 | Sommerich | 424/499 |
| 2010/0040687 A1 * | 2/2010 | Pedrozo et al. | 424/484 |

FOREIGN PATENT DOCUMENTS

WO   WO 96/39159   12/1996

OTHER PUBLICATIONS

Charulatha et al., Biomater., 24:759-767 (2003).*
Tierney et al (J. Mech. Behav. Biomed. Mater., 2(2):202-209 (2009).*
Vascular Solutions, D-Stat (2009).*
Biomaterials, 1980, Winter et al., (Eds.), John Wiley & Sons, New York, pp. 669-676.
Charulatha and Rajaram, "Influence of different crosslinking treatments on the physical properties of collagen membranes." 2003, Biomaterials. 24(5):759-767.
Collagen, 1988, vol. III, Biotechnology; Nimni, (Ed.), CRC Press, Inc., pp. 209-221.
Elbjeirami et al., "Enhancing mechanical properties of tissue-engineered constructs via lysyl oxidase crosslinking activity." 2003, J Biomed Mater Res A.66(3):513-21.

(Continued)

*Primary Examiner* — Thomas J Visone
(74) *Attorney, Agent, or Firm* — Lerner, David, Littenberg, Krumholz & Mentlik, LLP

(57) ABSTRACT

The invention relates to hemostatic compositions and methods for promoting hemostasis. The invention also relates to hemostatic compositions and methods for promoting wound healing. In various embodiments, the hemostatic compositions comprise crosslinkable collagen molecules having a porosity controlled by the ratio of weight percent collagen solids to weight percent crosslinker when crosslinking the collagen. In other embodiments, the hemostatic compositions comprise crosslinkable collagen molecules having a porosity controlled by the temperature and rate of freezing when drying the composition during fabrication. In some embodiments, the compositions contain additional agents, including biological agents.

20 Claims, 20 Drawing Sheets

(56) References Cited

OTHER PUBLICATIONS

Ibusuki, et al., "Photochemically cross-linked collagen gels as three-dimensional scaffolds for tissue engineering." 2007, Tissue Eng. 13(8):1995-2001.

Liu et al., "Photochemical crosslinked electrospun collagen nanofibers: synthesis, characterization and neural stem cell interactions." 2010, J Biomed Mater Res A. 95(1):276-82.

Sweeney, et al, "Candidate cell and matrix interaction domains on the collagen fibril, the predominant protein of vertebrates." 2008, J. Biol. Chem. 30:21187-21197.

Wissink, et al., "Improved endothelialization of vascular grafts by local release of growth factor from heparinized collagen matrices." 2000, J Control Release 64(1-3):103-14.

O'Brien et al., "Influence of freezing rate on pore structure in freeze-dried collagen-GAG scaffolds." 2004 Biomaterials 25:1077-1086.

Yang et al., "Development of a recombinant human collagen-type III based hemostat." 2004, J Biomed Mater Res B Appl Biomater. 69(1):18-24.

* cited by examiner

FLOWABLE COLLAGEN-BASED HEMOSTAT AND METHODS OF USE

CROSS-REFERENCE TO RELATED APPLICATIONS

This application claims priority to U.S. Provisional Application No. 61/449,292 filed Mar. 4, 2011, which is hereby incorporated by reference herein in its entirety.

BACKGROUND OF THE INVENTION

Excessive bleeding or hemorrhaging has always been a significant issue with many medical or surgical procedures. Because of this, the medical industry has continuously sought new and improved products to inhibit bleeding in a patient, and methods of establishing hemostasis. In general, these hemostatic products and processes assist in the rapid initiation of a hemostatic plug formed through platelet activation, aggregation, adhesion and gross clot formation at a tissue target site.

A wide variety of hemostatic products are made from different base materials, such as collagen, gelatin, oxidized regenerated cellulose, fibers, gauze sponges and fibrin. These products are used in a wide variety of medical and surgical procedures. For example, microfibrillar collagen is used extensively for wide-area parenchyma bleeding and for laparoscopic procedures. Hemostatic sponges are used in surgical as well as dermatological applications where adherence to the wound site and ease of removal are important considerations.

A number of hemostatic collagen-containing devices have previously been described. For example, U.S. Pat. Nos. 5,428,024; 5,352,715; and 5,204,382 generally relate to fibrillar and insoluble collagens that have been mechanically disrupted to alter their natural physical properties. Injectable collagen compositions are described in U.S. Pat. Nos. 4,803,075 and 5,516,532. International application WO 96/39159 describes a collagen-based delivery matrix made of dry particles in the size range from 5 µm to 850 µm, where the particles are suspended in water and have a particular surface charge density. A bioactive agent is then incorporated in the matrix prior to administration to a patient. U.S. Pat. No. 5,196,185 describes a collagen preparation having a particle size from 1 µm to 50 µm useful as an aerosol spray to form a wound dressing. U.S. Pat. No. 7,320,962 describes a hemostatic composition having a population of crosslinked polymer (e.g. gelatin or collagen) integrated into a non-crosslinked polymer (e.g. gelatin or collagen) population, such that the non-crosslinked collagen dissolves at the wound site, releasing the crosslinked collagen to form a hemostatic hydrogel. U.S. Pat. Nos. 6,063,061; 6,066,325 and 6,706,690 also describe hemostatic compositions that include soluble and/or non-fibrillar collagen, with plasticizers and hemostatic agents, such as thrombin, integrated within the composition.

Collagen pads have also been used to improve wound healing or to stop bleeding, via platelet aggregation and activation, the formation of thrombin on the surface of activated platelets, and the formation of a hemostatic fibrin clot by the catalytic action of thrombin on fibrinogen. Hemostatic agents are typically added to the collagen pads. For example, in U.S. Pat. No. 4,600,574 a collagen based tissue adhesive combined with fibrinogen and factor XIII is described. The fibrinogen and factor XIII are combined with the collagen by impregnating the flat collagen material with a solution comprising fibrinogen and factor XIII, and lyophilizing the material. U.S. Pat. No. 5,614,587 describes bioadhesive compositions comprising crosslinked collagen using a synthetic hydrophilic polymer.

However, because no single device or process can meet the dynamic applications of the medical industry, there continues to be a need to provide alternative systems and methods for achieving hemostasis, particularly compositions that do not require the use of additional hemostatic agents, such as thrombin. Thus, there continues to be a need for flowable hemostatic compositions that can easily be delivered to tissue and establish hemostasis without delaying or inhibiting tissue repair. There is also a need for hemostatic compositions that promote wound healing; and hemostatic compositions that readily adhere to the tissue but not to surgical materials, such as gauze. The present invention satisfies this need.

SUMMARY OF THE INVENTION

The present invention relates to a hemostatic composition. The composition includes crosslinked collagen, wherein the composition has a porosity controlled by the ratio of percent collagen solids to percent crosslinker when crosslinking the collagen. In one embodiment, the hemostatic composition has a porosity greater than about 50% and a surface area of between about 0.5 to about 30 $m^2/g$. In another embodiment, the crosslinked collagen includes at least one material structure from the group consisting of fibers, ribbons, ropes and sheets. In another embodiment, the number of structures is controlled by the ratio of percent collagen solids to percent crosslinker when crosslinking the collagen. In another embodiment, the number of structures is controlled by the collagen concentration prior to freezing the collagen. In another embodiment, the number of structures is controlled by the temperature and rate of freezing when the collagen is lyophilized. In another embodiment, the collagen is microfibrillar collagen. In another embodiment, the collagen is fibrillar collagen. In another embodiment, the hemostatic composition includes at least one biological agent. In another embodiment, the at least one biological agent comprises thrombin. In another embodiment, the crosslinked collagen is in a physiologically acceptable liquid vehicle. In another embodiment, the liquid vehicle is water, saline, calcium chloride or a combination thereof. In another embodiment, the composition is flowable, such that it can be easily dispensed from a syringe having at least a 1.6 mm opening.

The present invention also includes a method of fabricating a flowable hemostatic composition. The method includes the steps of crosslinking about 0.1-10% collagen with a crosslinking agent at a ratio between about 7.5:1 to 500:1, lyophilizing the crosslinked collagen until dried, and reconstituting the crosslinked collagen at a concentration of about 50-200 mg/mL. In one embodiment, the crosslinking agent is glutaraldehyde. In another embodiment, the collagen is microfibrillar collagen. In another embodiment, the collagen is fibrillar collagen. In another embodiment, the crosslinked collagen is reconstituted in a physiologically acceptable liquid vehicle. In another embodiment, the liquid vehicle is water, saline, calcium chloride or a combination thereof. In another embodiment, the method further includes the step of adding at least one biological agent. In another embodiment, the at least one biological agent comprises thrombin. In another embodiment, the method further includes the step of controlling the porosity of the crosslinked collagen by controlling the temperature and rate of freezing during lyophilization. In another embodiment, the method further includes the step of controlling the porosity by controlling the collagen concentration prior to freezing the collagen. In another embodiment, the method further includes the step of controlling the material structure of the crosslinked collagen by controlling the temperature and rate of freezing during lyophilization. In another embodiment, the material structure includes at least one from the group consisting of fibers, ribbons, ropes and sheets.

The present invention also includes a hemostatic composition formed by the steps of crosslinking about 0.1-10% collagen with glutaraldehyde at a ratio between about 7.5:1 to 500:1, lyophilizing the crosslinked collagen until dried, and reconstituting the crosslinked collagen at a concentration of about 50-200 mg/mL.

The present invention also includes a wound healing composition. The composition includes crosslinked collagen at a concentration of between about 50-200 mg/mL, wherein the composition has a porosity controlled by the ratio of percent collagen solids to percent crosslinker when crosslinking the collagen.

The present invention also includes a composition comprising crosslinked collagen, wherein the composition has a porosity controlled by the temperature and rate of freezing used to manufacture the composition.

The present invention also includes a composition comprising crosslinked collagen, wherein the composition is flowable such that it can be easily dispensed from a syringe and where the flowability is controlled by the presence of at least one material structure from the group consisting of fibers, ribbons, ropes and sheets.

The present invention also includes a method of promoting hemostasis at a bleeding site comprising applying a hemostatic composition to the bleeding site, wherein the hemostatic composition includes crosslinked collagen having a porosity controlled by the ratio of percent collagen solids to percent crosslinker when crosslinking the collagen.

The present invention also includes a method of promoting wound healing at an injury site includes applying to the injury site a composition of about 1-5% crosslinked collagen that has been lyophilized and reconstituted at a concentration of about 50-200 mg/mL.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIG. 2A is a general method for fabricating a hemostatic composition; FIG. 2B is an exemplary method of fabricating a hemostatic composition using glutaraldehyde as a crosslinker; FIG. 2C is an exemplary method of fabricating a hemostatic composition using EDC/NHS as a crosslinker.

FIGS. 3A-3D, is an SEM image at a magnification of 500× of 1% collagen samples. FIG. 3A is a non-crosslinked control, and FIGS. 3B-3D are samples crosslinked with glutaraldehyde (GTA) for 4 hours at 500:1 (FIG. 3B), 250:1 (FIG. 3C) and 100:1 (FIG. 3D), frozen at −28° C. and lyophilized until dry.

FIGS. 4A-4C, is an SEM image at a magnification of 250× of 1% collagen crosslinked at a ratio of 100:1. Collagen pellets of 1% collagen crosslinked at 100:1 were frozen at −28° C. (FIG. 4A), at −80° C. (FIG. 4B) or in liquid nitrogen (FIG. 4C) and lyophilized until dry.

FIGS. 5A-5C, is an SEM image at a magnification of 500× of 1% collagen crosslinked at a ratio of 100:1. Collagen pellets of 1% collagen crosslinked at 100:1 were frozen at −28° C. (FIG. 5A), at −80° C. (FIG. 5B) or in liquid nitrogen (FIG. 5C) and lyophilized until dry.

FIGS. 6A-6C, is an SEM image at a magnification of 1000× of 1% collagen crosslinked at a ratio of 100:1. Collagen pellets of 1% collagen crosslinked at 100:1 were frozen at −28° C. (FIG. 6A), at −80° C. (FIG. 6B) or in liquid nitrogen (FIG. 6C) and lyophilized until dry.

FIGS. 7A-7C, is an SEM image at a magnification of 50× of 1% collagen crosslinked at 100:1, which were ground using 3×3 sec pulses, and reconstituted at 150 mg/mL. Samples were frozen at −28° C. (FIG. 7A), at −80° C. (FIG. 7B) or in liquid nitrogen (FIG. 7C) prior to lyophilizing (until dry), grinding and reconstitution.

FIGS. 8A-8C, is an SEM image at a magnification of 250× of 1% collagen crosslinked at 100:1, which were ground using 3×3 sec pulses, and reconstituted at 150 mg/mL. Samples were frozen at −28° C. (FIG. 8A), −80° C. (FIG. 8B) or in liquid nitrogen (FIG. 8C) prior to lyophilizing (until dry), grinding and reconstitution.

FIGS. 9A-9C, is an SEM image at a magnification of 1000× of 1% collagen crosslinked at 100:1, which were ground using 3×3 sec pulses, and reconstituted at 150 mg/mL. Samples were frozen at −28° C. (FIG. 9A), at −80° C. (FIG. 9B) or in liquid nitrogen (FIG. 9C) prior to lyophilizing (until dry), grinding and reconstitution.

FIGS. 10A-10D, is an SEM image of structural differences in crosslinked collagen materials. The primary material structures are fibers (A), ribbons (B), ropes (C) and sheets (D).

FIGS. 11A and 11B, is an SEM image of glutaraldehyde crosslinked microfibrillar collagen materials (250:1) lyophilized at a freezing rate of −1° C./min (A) and a freezing rate of −0.5° C./min (B). Images are at 500× magnification.

FIGS. 12A-12D, is an SEM image of lyophilized glutaraldehyde crosslinked microfibrillar collagen materials (250:1) undiluted (A), and diluted by volume in USP water at 1:1 collagen (B), 1:5 collagen (C) and 1:10 collagen (D).

FIGS. 13A-13B, is an SEM image at a magnification of 500× of 1% collagen (FIG. 13A) and Surgiflo® (FIG. 13B) after hemostasis had been achieved through application of the material to a bleeding site.

FIGS. 14A-14C, is an SEM image of 5% collagen (FIG. 14A, 1500×), Floseal® (FIG. 14B, 1500×), and Surgiflo® (FIG. 14C, 1000×) after hemostasis had been achieved through application of the material to a bleeding site.

FIGS. 15A-15B, is an SEM image at a magnification of 3000× of 1% collagen (FIG. 15A) and 5% collagen without the addition of thrombin (FIG. 15B) after hemostasis had been achieved through application of the material to a bleeding site.

FIGS. 16A-16D, is a histology section at a magnification of 20× of collagen samples in a liver defect. FIG. 16A is 0.1% fibrillar collagen crosslinked at a ratio of 40:1, FIG. 16B is 1% fibrillar collagen crosslinked at a ratio of 25:1, FIG. 16C is 1% microfibrillar collagen crosslinked at a ratio of 250:1, and FIG. 16D is Floseal®.

FIGS. 17A-17C, is a histology section at a magnification of 10× of collagen samples shown at the material/tissue interface 8 weeks after implantation. FIG. 17A is 1% microfibrillar collagen crosslinked at a ratio of 100:1, FIG. 17B is 1% microfibrillar collagen crosslinked at a ratio of 250:1, and FIG. 17C is 0.1% fibrillar collagen crosslinked at a ratio of 10:1.

FIG. 18A-18E, is an SEM image of EDC/NHS crosslinked collagen at 500× magnification, FIG. 18A is a EDC/NHS Control; FIG. 18B is material crosslinked at half the EDC/NHS concentration relative to the control; FIG. 18C is material crosslinked at two times the EDC/NHS concentration relative to the control; FIG. 18D is material crosslinked using EDC/NHS chemistry for 2 hours; and FIG. 18E is material crosslinked for 16 hours using EDC/NHS chemistry.

DETAILED DESCRIPTION

Figure 1:
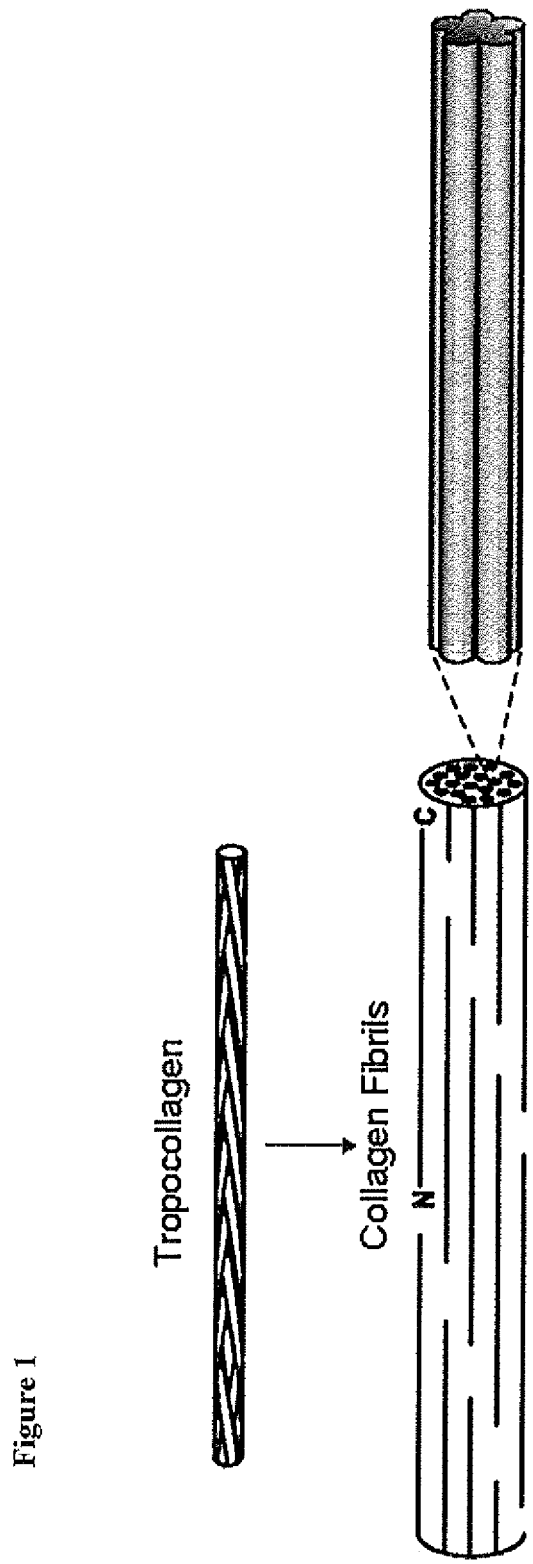
FIG. 1 is an illustration of the formation of insoluble fibrillar collagen structures from tropocollagen. Triple helical tropocollagen, which is soluble at a low pH, forms a staggered fibrillar structure which is substantially insoluble in water as pH is increased.

The present invention relates generally to hemostatic compositions and methods for promoting hemostasis. Preferably, the present invention relates to flowable, hemostatic compositions that are collagen-based, and provides for the precise, localized placement of the hemostatic composition (or device) in an actively bleeding site, such that the device remains localized therein to establish hemostasis. The invention also relates to hemostatic compositions and methods for promoting wound healing. In various embodiments, the hemostatic compositions comprise crosslinkable collagen molecules suitable for promoting hemostasis or wound healing. In some embodiments, the compositions optionally include a biological agent, such as thrombin. In certain embodiments, the time needed to establish hemostasis is less than about 10 minutes in an actively bleeding site. In preferred embodiments, the time needed to establish hemostasis is less than about 2 minutes in an actively bleeding site. Hemostasis can be established within this timeframe with or without the use of the additional biological agents.

The hemostatic composition of the present invention can further be used in a variety of applications where known surgical hemostats and sealants have been used. For example, the present invention can be used as a surgical hemostat or sealant, a wound repair adhesive, a soft tissue augmenter and a soft tissue substitute. In some embodiments, greater surface area is desirable for establishing rapid hemostasis by creating an optimized platform for platelet adhesion and clot stabilization. In certain embodiments, the compositions of the present invention are both hemostatic and promote wound healing.

Swelling characteristics of the compositions of the present invention are dependent not only on the material forming the composition (collagen), but also on the porosity of the composition and the extent of crosslinking. Thus, swelling characteristics of the compositions can be controlled by controlling the porosity of the composition and the extent of crosslinking. In preferred embodiments, swelling of the composition is optimized to promote hemostasis, yet prevent the composition from impinging on the surrounding tissues.

The porosity of the composition can be manipulated by the temperature and/or the rate of freezing during the drying process. Porosity can also be manipulated according to the crosslinking ratio used in the crosslinking step during fabrication.

Definitions

The definitions used in this application are for illustrative purposes and do not limit the scope of the invention.

The articles "a" and "an" are used herein to refer to one or to more than one (i.e. to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

"Equivalent," as used herein, may refer to a mass ratio. For example, if using one grain of collagen, then one equivalent would be one gram of another material, such as a crosslinking agent.

"Collagen", as used herein; refers to a natural polymer derived from connective tissue. Although collagen can take many forms: partially denatured and sometimes partially fragmented; monomeric with a native triple helical conformation as in procollagen; polymerized into a five-mer aggregate as in microfibrillar collagen; or polymerized into higher-ordered cable-like fibrils as in fibrillar collagen, a "collagen molecule" may be taken to describe any of these entities or molecular forms of collagen as described herein throughout.

Fiber-like structures that are not greater than 30 µm in diameter are known as "fibers". "Ropes" are bundles of fibers. "Ribbons" are described as structures that are smooth and flat with a width that is greater than a fiber width. Structures that are not fibers, ropes or ribbons that are flat are called "sheets".

"Glutaraldehyde" (GTA), as used herein, is a compound containing two equally reactive aldehyde groups that can each react with an amine to chemically crosslink collagen.

"N-(3-dimethylaminopropyl)-N'-ethylcarbodiimide hydrochloride" (EDC) and "N-hydroxysuccinimde" (NHS), as used herein, refers to two compounds that, when used in combination, react synergistically to chemically crosslink a carboxylic acid group and an amine group in collagen.

"Sodium hydroxide" (NaOH), as used herein, is a base that, when diluted, can be used to help increase the pH of a solution.

"Hydrochloric acid" (HCl), as used herein, is an acid that can be diluted and used to help lower the pH of a solution.

"Percent (%) solids", as used herein, is expressed as mg material per mL. For example, 1% solids is approximately 10 mg/mL.

"Crosslinking", as used herein, refers to the joining of at least two molecules (such as, for example, collagen), to each other by at least one physical or chemical means, or combinations thereof.

"Isolated" means altered or removed from the natural state. For example, a peptide naturally present in a living animal is not "isolated," but the same peptide partially or completely separated from the coexisting materials of its natural state is "isolated." An isolated protein can exist in substantially purified form, or can exist in a non-native environment.

"Naturally occurring" as used herein describes a composition that can be found in nature as distinct from being artificially produced. For example, collagen present in an organism, which can be isolated from a source in nature and which has not been intentionally modified by a person in the laboratory, is naturally occurring.

The terms "diminish" and "diminution," as used herein, means to reduce, suppress, inhibit or block an activity or function by at least about 10% relative to a comparator value. Preferably, the activity is suppressed, inhibited or blocked by 50% compared to a comparator value, more preferably by 75%, and even more preferably by 95%.

The terms "effective amount" and "pharmaceutically effective amount" refer to a nontoxic but sufficient amount of an agent to provide the desired biological result. The desired biological result can be reduction and/or alleviation of the signs, symptoms, or causes of a disease or disorder, the reduction of bleeding, wound healing or any other desired alteration of a biological system. An appropriate effective amount in any individual case may be determined by one of ordinary skill in the art using routine experimentation.

An "individual", "patient" or "subject" as used herein, includes a member of any animal species. Such animal species include, but are not limited to, birds, humans and other primates, and other mammals including commercially relevant mammals such as cattle, pigs, horses, sheep, cats, and dogs.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types, "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "treatment" as used within the context of the present invention is meant to include therapeutic treatment as well as prophylactic, or suppressive measures for the disease or disorder, the reduction of bleeding, increased rate of wound healing or any other desired alteration of a biological system. Thus, for example, the term treatment includes the administration of a composition prior to or following the onset of bleeding, thereby establishing hemostasis.

As used herein, an "instructional material" includes a publication, a recording, a diagram, or any other medium of expression which can be used to communicate the usefulness of a compound, composition, formulation or delivery system of the invention in the kit for affecting the conditions recited herein. For example, the instructional material can describe one or more methods of reducing bleeding at a targeted treatment site. The instructional material of the kit of the invention can, for example, be affixed to a container which contains the identified compound, composition, formulation, or delivery system of the invention or be shipped together with a container which contains the identified compound, composition, formulation, or delivery system. Alternatively, the instructional material can be shipped separately from the container with the intention that the instructional material and the compound be used cooperatively by the recipient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Collagen-Based Hemostatic Compositions

The hemostatic compositions of the present invention are formed primarily of collagen crosslinked with a crosslinking agent, such as glutaraldehyde. In some embodiments, EDC and NHS, or other carbodiimides may be used to crosslink collagen. In yet other embodiments, transglutaminase, genipin or an avidin-biotin interaction may be used, alone or in combination with other crosslinkers, to crosslink collagen molecules in the compositions. The compositions may optionally include a biological agent, such as thrombin. The compositions may also optionally include additional polymers, such as polyethylene glycol. In a preferred embodiment, the composition of the present invention is comprised predominantly of collagen due to the superior hemostatic properties of collagen versus other materials such as gelatin, Crosslinkable Collagen Collagen, preferably hypoallergenic collagen, is present in the composition in an amount sufficient to provide hemostatic activity, as well as to thicken the composition and augment its cohesive properties. In addition to thickening the composition, the collagen acts as a macromolecular lattice or scaffold. This feature gives more strength and durability to the resulting clot. The collagen may be a telopeptide collagen or telopeptide collagen (e.g., native collagen). For example, the collagen used as a starting material may be derived from collagen collected from any number of mammalian sources, such as bovine, porcine and human. In another example, the collagen may come from any source, including corium collagen, tendon collagen, and collagen flour. It should be appreciated that the present invention is not limited to any particular type and/or source of collagen.

The collagen molecule preferably comprises at least one crosslinkable moiety that is able to form a bond, directly or indirectly, with another crosslinkable moiety on another collagen molecule. Any crosslinkable moieties known in the art may be used. By way of non-limiting examples, the collagen molecules can be crosslinked by covalent interactions, by non-covalent interactions, by thermally reversible interactions, by ionic interactions, or by combinations thereof. These moieties can be crosslinked by physical, chemical, thermal, or photoinitiation (e.g., visible, UV) means, or by any combination thereof. The initial amount of collagen suitable for the crosslinking steps of the present invention may be equal to or less than about 5% solids. In other embodiments, the amount of collagen is between about 0.1-10% solids. In still other embodiments, the amount of collagen is between about 0.3-5% solids. In one preferred embodiment, the amount of collagen is about 1% solids. In another preferred embodiment, the amount of collagen is about 0.1-5% solids.

One form of collagen which is employed may be described as at least "near native" in its structural characteristics. In various embodiments, the collagen may be characterized as resulting in insoluble fibers at a pH above 5. In some embodiments, the collagen comprises fibers having diameters in the range of from about 10 to about 500 inn and there will be substantially little, if any, change in the helical structure. In certain embodiments, the majority of the fibers have diameters in the range of from about 20 to about 100 nm. In addition, the collagen must be able to enhance gelation in a surgical sealant composition. In preferred embodiments, the starting collagen material is microfibrillar type I collagen. In other embodiments, the starting collagen material is fibrillar collagen. Other form of collagen which are employed may include microfibrillar collagen mixed with at least partially denatured collagen or gelatin. Although collagen can take many forms: denatured and sometimes partially fragmented; monomeric with a native triple helical conformation as in procollagen; polymerized into a five-mer aggregate as in microfibrillar collagen; or polymerized into higher-ordered cable-like fibrils as in fibrillar collagen, a "collagen molecule" may be taken to describe any of these entities or molecular forms of collagen as described herein throughout.

As contemplated herein, microfibrillar collagen may be used and may further provide several advantages in selected applications. For example, microfibrillar collagen has a strong platelet activating activity owing to its ability, via the presence of glycine-proline-hydroxyproline repeats and integrin binding sites in its triple helical domain, to ligate and activate platelet GPVI and $\alpha 2\beta 1$ integrin receptors. Second, microfibrillar collagen assembles into collagen fibrils which provide a rigid substrate and mesh-like network to support platelet adhesion and clot stabilization. Third, during clot dissolution and wound healing, microfibrillar and fibrillar collagen bind cells and growth and differentiation factors, thereby serving as an ideal substrate for tissue regeneration.

In another embodiment, collagen in solution is used in the generation of collagen for the hemostatic composition. Collagen in solution (CS) consists of triple helical tropocollagen which is soluble at a low pH (such as around 2). Increasing the pH allows the collagen fibers to interact through hydrogen bonding, thereby forming a microfibrillar structure. As a result of adjusting the pH (using NaOH and/or HCl) to approximately 6.5-8 and optionally adding calcium ions (or similar charged particles or ions) during precipitation, the microfibrils begin to associate and form a staggered fibrillar structure which is substantially insoluble in water, as depicted in FIG. 1 (adapted from Sweeney, et al, *J. Biol. Chem.* 2008, 30, 21187-21197). This is due to a combination of electrostatic interactions and increasing molecular weight. The increase in pH upon precipitation causes the carboxylic acid groups to be deprotonated, which gives an overall neutral charge to fibrils. The association of the fibers into larger fibrillar structures that are tightly bound, and have a net charge close to neutral, increases the repulsion of water thereby helping to decrease the solubility of collagen fibrils.

The amount of the collagen in the hemostatic composition can be varied to provide hemostats of differing viscosities and strengths, depending on the particular application. In some embodiments, the collagen is a flowable composition dispersed in saline to provide a final concentration in the composition (reconstituted) of less than or equal to about 200 mg/mL. In other embodiments, the reconstituted concentration is between about 50-250 mg/mL. In still other embodiments, the reconstituted concentration is between about 100-200 mg/mL. It should be appreciated that any concentration of collagen may be used, provided the collagen continues to provide hemostatic activity, and remains sufficiently flowable so as to be administered via a syringe, preferably having an opening of at least 1.6 mm. Any type of syringe suitable for carrying 1 cc to 20 cc of material can be used, such as 5 to 6 cc, and 10 to 12 cc of material.

Crosslinking Agents

After precipitating collagen and diluting to the desired concentration, a second processing step is carried out to crosslink the collagen. Crosslinking, such as with glutaraldehyde (GTA) or other aldehydes, makes the collagen substantially insoluble by forming covalent bonds, which are not easily broken, between collagen fibrils. During this crosslinking step, the GTA forms covalent bonds between crosslinkable moieties, such as between amine groups, and possibly some carboxylic acid groups, in the amino acids in collagen. This forms a matrix of fibrillar collagen, by formation of covalent bonds that are more difficult to break than weaker hydrogen bonds, thereby resulting in a substantially insoluble crosslinked material. Other methods for crosslinking collagen with glutaraldehyde are described in U.S. Pat. Nos. 4,582,640 and 4,642,117, the disclosures of which are incorporated by reference herein.

In some embodiments, a transglutaminase is used to crosslink collagen molecules. Transglutaminases are known to catalyze the formation of covalent bonds between a free amine group (e.g., protein-bound lysine) and the gamma-carboxamide group of protein-glutamine. Bonds formed by transglutaminase are highly resistant to proteolytic degradation. Non-limiting examples of transglutaminases useful in the compositions and methods of the invention include Factor XIII and *Streptomyces mobaraensis* transglutaminase (e.g., Activa TG™). In other embodiments, genipin or an avidin-biotin interaction may be used, alone or in combination with other crosslinkers; to crosslink collagen molecules in the compositions and methods of the invention. In certain embodiment, lysyl oxidase (LO) may be employed. LO is a copper-dependent amine enzyme (oxidase) that crosslinks extracellular collagen by catalyzing the formation of covalent bonds between the aldehydes from lysyl and hydroxylysyl side chains. In this manner, cells could be transfected with LO to crosslink collagen.

In additional embodiments, carbodiimides such as N-(3-dimethylaminopropyl)-N'-ethylcarbodiimide hydrochloride (EDC) and N-hydroxysuccinimide (NHS) may be used to catalyze a crosslinking reaction between collagen molecules. EDC/NHS is known to form chemical bonds between a free amine group and a carboxylic acid group. EDC and NHS facilitate the reaction between the two functional groups but do not remain in the final crosslinked material; as a result EDC/NHS is referred to as a "zero length" crosslinker. This reduces the risk of adverse reactions because the resultant material is composed only of collagen. The highly water soluble compounds EDC and NHS are removed during washing steps and do not remain in the crosslinked collagen material. For example, crosslinking at a concentration of about 0.4-0.5% collagen can be achieved with EDC and NHS at a ratio between 850 mg EDC (4.5 mmol) and 210 mg NHS (1.8 mmol) to 3.7 g EDC (18 mmol) and 840 mg NHS (7.2 mmol).

Acyl azide, and diimidoesters (such as dithiobispropionimidate (DTBP), dimethyl suberimidate (DMS) and 3,3'dithiobispropionimidate (DTBP) are other chemical crosslinking agents for collagen. Alternatively, dry heat (DHT), UV irradiation and photochemical crosslinking including photo initiators may be used separately or in combination with other crosslinkers described herein. For example, photo initiators may include Rose Bengal or riboflavin.

In some embodiments, crosslinking of collagen may be carried out before use of the formulation for hemostasis; while in other embodiments, crosslinking may be carried out at the time of application while the formulation is being used for hemostasis. The above examples are non-limiting. It should be understood that various other materials used to crosslink collagen may be used.

Material Fabrication

Figure 2A:
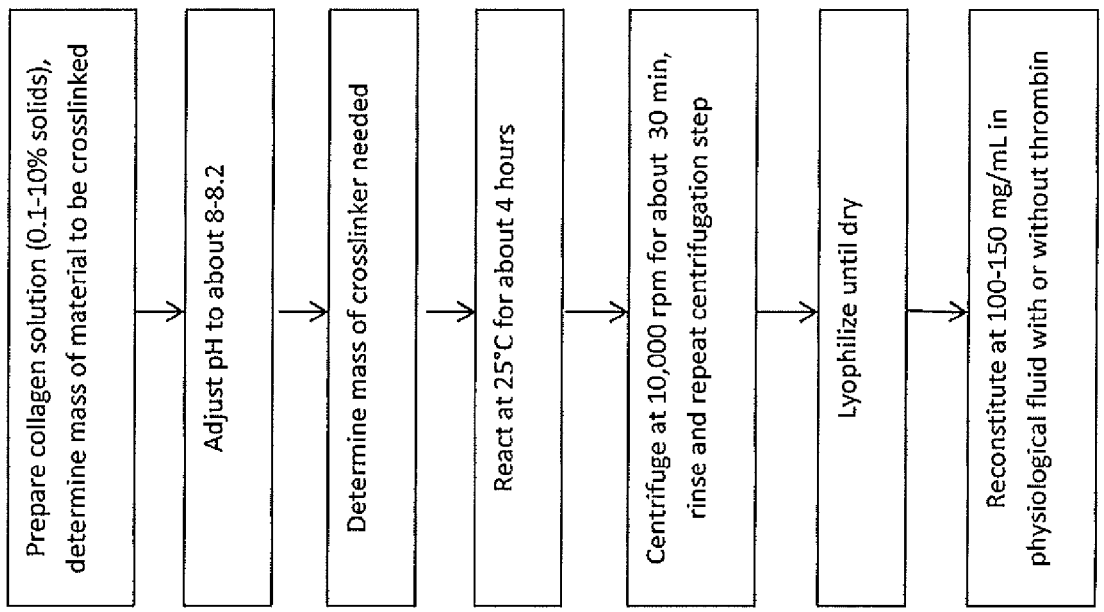
FIGS. 2A-2C, is a set of flowcharts for exemplary methods of fabricating a hemostatic composition of the present invention.
Figure 2B:
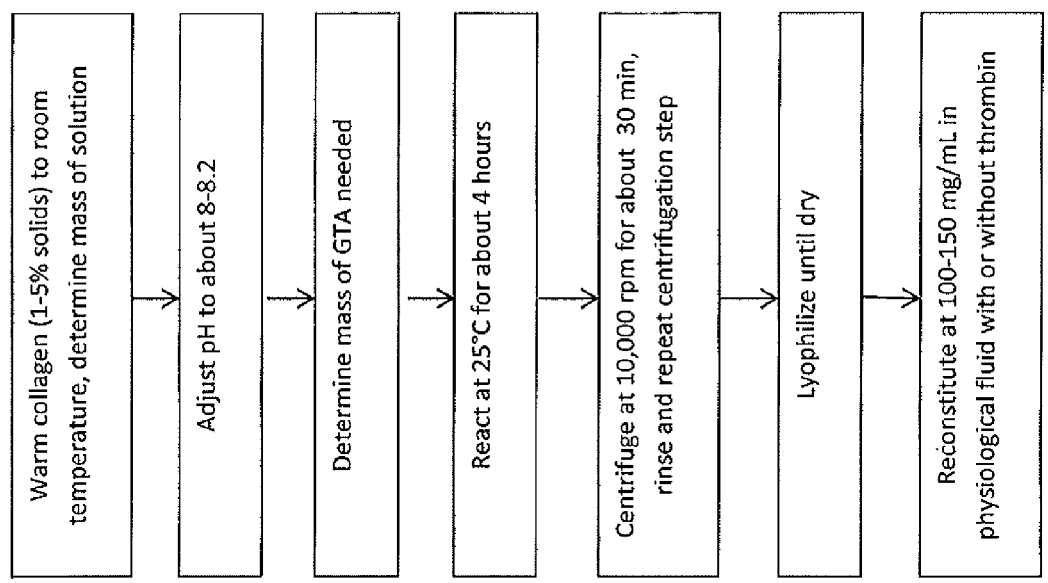
Figure 2C:
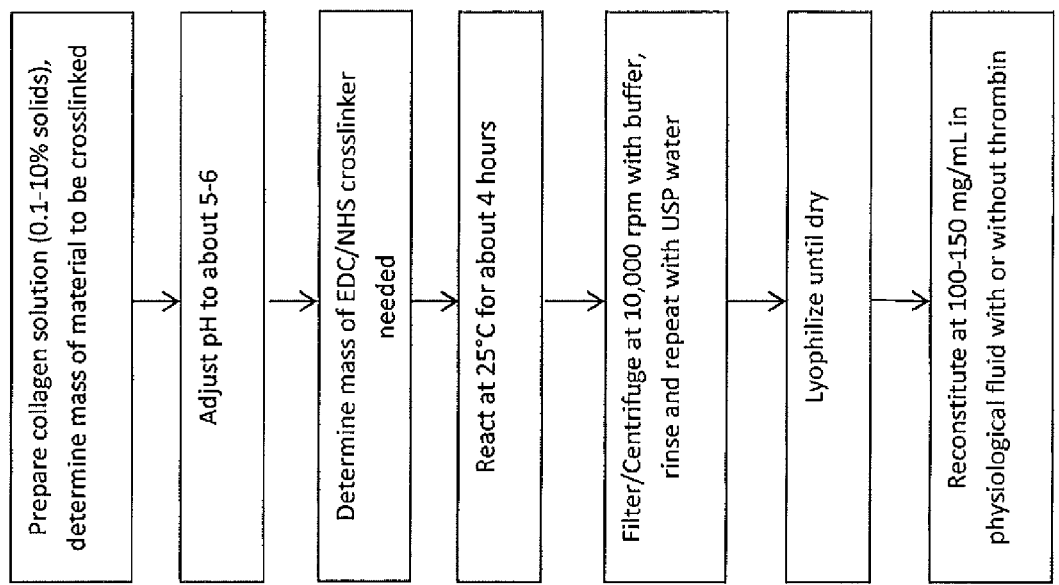

As contemplated herein, the collagen-based hemostatic compositions of the present invention may be manufactured according to the following steps, and as outlined in the flowcharts of FIG. 2. FIG. 2A provides a general method for fabricating a hemostatic composition. FIG. 2B provides an exemplary method of fabricating a hemostatic composition using glutaraldehyde as a crosslinker. FIG. 2C provides an exemplary method of fabricating a hemostatic composition using EDC/NHS as a crosslinker.

First, collagen in solution is precipitated using a buffer then centrifuged to obtain a collagen pellet that can be diluted with USP water to a desired concentration. Next, the collagen is crosslinked to create a substantially insoluble material that is capable of achieving hemostasis. The concentration of collagen used during the crosslinking step is termed "percent solids" and is based on the mass of collagen per volume of liquid, for example 10 mg/mL collagen would be 1% solids. Preferably, the process utilizes a concentration of about 1% solids during crosslinking.

The ratio of crosslinking agent, such as glutaraldehyde, to collagen may vary. Prior to the addition of GTA, the pH is adjusted to between about 6-11, and preferably between about 7-10. In one preferred embodiment, the pH is adjusted between 8.0-8.2, to create optimal conditions for the crosslinking reaction. The mass of glutaraldehyde (GTA) used is relative to the mass of collagen, and may be written as a ratio of percent solids:percent crosslinker. For example, 1% solids to 0.01% GTA would be a crosslinking ratio of 100:1. As contemplated herein, ratios from 7.5:1 to 500:1 may be used. As described herein, a ratio of 7.5:1 is referred to as a high crosslink ratio (having a high crosslink density with many crosslinked molecules); and a ratio of 500:1 is referred to as a low crosslink ratio (having a low crosslink density with fewer crosslinked molecules). The crosslink ratio in turn affects the physical and chemical properties of the material, including solubility. Table 1 below outlines the mass of each material required for crosslinking microfibrillar collagen at various ratios of solids to GTA. Table 2 outlines the mass of each material required for crosslinking fibrillar collagen at various ratios of solids to GTA.

TABLE 1

Mass of materials required for crosslinking of microfibrillar collagen

| Crosslinking ratio (solids:GTA) | Crosslinking ratio | Concentration of collagen (mg/mL) | Percent solids | Mass of collagen solution (g) | Mass collagen (g) | Mass of 25% GTA Solution (g) |
|---|---|---|---|---|---|---|
| 250:1 | 0.004 | 10 | 1 | 3000 | 30 | 0.48 |
| 100:1 | 0.010 | 10 | 1 | 3000 | 30 | 1.2 |
| 75:1 | 0.013 | 10 | 1 | 3000 | 30 | 1.6 |
| 50:1 | 0.020 | 10 | 1 | 3000 | 30 | 2.4 |
| 100:1 | 0.010 | 50 | 5 | 3000 | 150 | 6.0 |
| 75:1 | 0.013 | 50 | 5 | 3000 | 150 | 8.0 |
| 50:1 | 0.020 | 50 | 5 | 3000 | 150 | 12.0 |

TABLE 2

Mass of materials required for crosslinking of fibrillar collagen.

| Crosslinking ratio (solids:GTA) | Crosslinking ratio | Concentration of collagen (mg/mL) | Percent solids | Mass of collagen solution (g) | Mass collagen (g) | Mass of 25% GTA Solution (g) |
|---|---|---|---|---|---|---|
| 40:1 | 0.025 | 1 | 0.1 | 3000 | 3 | 0.30 |
| 25:1 | 0.04 | 1 | 0.1 | 3000 | 3 | 0.48 |
| 10:1 | 0.1 | 1 | 0.1 | 3000 | 3 | 1.2 |
| 7.5:1 | 0.13 | 1 | 0.1 | 3000 | 3 | 1.6 |
| 40:1 | 0.025 | 10 | 1 | 3000 | 30 | 3.0 |
| 25:1 | 0.04 | 10 | 1 | 3000 | 30 | 4.8 |
| 10:1 | 0.1 | 10 | 1 | 3000 | 30 | 12.0 |

When using EDC/NHS as the crosslinking agents a buffer solution of 2-morpholinoethane sulfonic acid (MES) is used to provide the optimal reaction conditions. This solution provides a pH between 5-6. The volume of buffer used is relative to the mass of collagen used, preferably a solution concentration of 0.4-0.5% collagen is created, and more preferably the collagen solution in MES is between 0.45-0.47%. The mass of EDC and NHS used in the crosslinking reaction are also relative to mass of collagen used. The mass equivalents of EDC relative to collagen are between 0.8-3.5 and the mass equivalents of NHS relative to collagen are between 0.2-0.8. Preferably 0.8-1.7 equivalents of EDC are used and 0.2-0.42 equivalents of NHS are used. After the material is crosslinked, it is lyophilized (freeze-dried) to remove water. As contemplated herein, the various structures and properties of the resulting formulated collagen materials can be customized or otherwise selected for. For example, altering freezing parameters such as temperature, temperature gradients, and time of freezing at one or more temperatures or temperature gradients allows for the selection and/or control of the final product properties. A freezing time of 2 to 6 hours at various freezing rates (range of instantaneous (e.g., liquid nitrogen) to $-0.1°$ C./min) with a primary drying cycle at temperatures between 0 and 15° C. ranging from 1 to 24 hours and secondary drying cycle at temperatures between 20 and 40° C. ranging from 2 to 10 hours.

Figure 10:
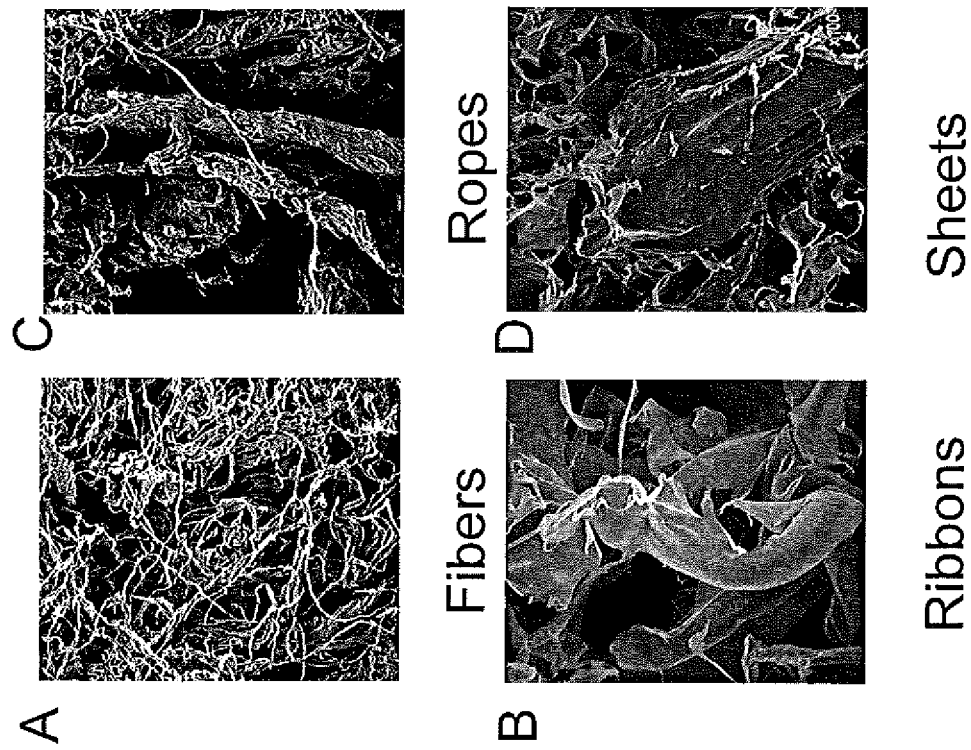
FIG. 10, comprising

The dried material resembles a scaffold that is porous and can be ground or cut into smaller pieces of a desired size (such as approximately 2.5×2.5 mm cubes or smaller) for filling into an applicator, such as a syringe. The crosslinked collagen material is white or may have a yellow tint upon reconstitution in physiologic fluid. As demonstrated herein, there are four primary material structures that can affect the reconstitution and handling properties of the resulting collagen materials of the present invention. As shown in FIG. 10, these structures including fibers (FIG. 10A), ribbons (FIG. 10B), ropes (FIG. 10C) and sheets (FIG. 10D). Porosity can also provide a similar effect.

The collagen pellet can be diluted or reconstituted to create a flowable composition. In various embodiments, the collagen is reconstituted in a physiologically acceptable liquid vehicle, such as an aqueous isotonic vehicle at about a physiologic salt concentration. Without limitation, the solution can be water, USP water, saline, calcium chloride or other physiologically acceptable fluid. The collagen and diluting solution can be mixed using any methods as would be understood by those skilled in the art, until the solution is substantially homogeneous. For example, the collagen can be mixed within the applicator. The final concentration of reconstituted collagen can vary, and may generally fall within the range of between about 50-250 mg/mL, and preferably between about 100-200 mg/mL.

Optional Biological Agents

A biological agent can optionally be incorporated into the compositions of the present invention. In some embodiments, the biological agent is mixed into a solution or suspension comprising the crosslinkable collagen. In some embodiments, the biological agent is physically incorporated into the crosslinked collagen composition just prior to application to the patient or subject. In other embodiments, the biological agent is incorporated while reconstituting the lyophilized and cut collagen particles, or even prior to lyophilization. In still further embodiments, the biological agent is incorporated in the form of a microsphere.

Biological agents may be any of several classes of compound. For example, where the biological agents are proteins, peptides, or polypeptides, they may be derived from natural materials, or be materials produced by recombinant DNA technology, or mutants of natural proteins, peptides, or polypeptides, or produced by chemical modification of proteins, peptides, or polypeptides. It should be appreciated that the classes of biological agents listed herein, and the particular exemplars of each class, are to be considered as exemplary, rather than limiting. Biological agents may, for example, be members of the natural coagulation pathway ("coagulation factors"). Such proteins include, by way of non-limiting examples, tissue factors, factors VII, VIII, IX, and XIII, fibrin, and fibrinogen.

A biological agent may also be a protein or other compound that activates or catalyzes the natural pathways of clotting ("coagulation activators"). These include, for example, thrombin, thromboplastin, calcium (e.g. calcium glucuronate), bismuth compounds (e.g. bismuth subgallate), desmopressin and analogs, denatured collagen (gelatin), chitosan and fibronectin. Vitamin K may contribute to activation of coagulation. In preferred embodiments, the addition of exogenous coagulation activators is not necessary.

A biological agent may act by activating, aggregating or stimulating platelets ("platelet activators"), including, for example, cycloheximide, N-monomethyl L-arginine, atrial naturetic factor (ANF), small nucleotides (including cAMP, cGMP, and ADP), prostaglandins, thromboxanes and analogs thereof, platelet activating factor, phorbols and phorbol esters, ethamsylate, and hemoglobin. Nonabsorbable powders such as talc, and denatured or surface-absorbed proteins can also activate platelets.

A biological agent may act by local vasoconstriction ("vasoconstrictors"), such as, by way of non-limiting examples, epinephrine (adrenaline), adrenochrome, tetrahydrozoline, antihistamines (including antazoline), oxymetazoline, vasopressin and analogs thereof, and cocaine.

A biological agent may act by preventing destruction or inactivation of clotting reactions ("fibrinolysis inhibitors"), including, by way of non-limiting examples, eosinophil major basic protein, aminocaproic acid, tranexamic acid, aprotinin (Trasylol™), plasminogen activator inhibitor, plasmin inhibitor, alpha-2-macroglobulin, and adrenoreceptor blockers.

Thrombin acts as a catalyst for fibrinogen to provide fibrin, an insoluble polymer. In some embodiments, thrombin is present in the composition in an amount sufficient to catalyze polymerization of fibrinogen present in a patient's plasma. Thrombin also activates FXIII, a plasma protein that catalyzes covalent crosslinks in fibrin, rendering the resultant clot insoluble. In certain embodiments, thrombin may be present in the composition in a concentration of from about 0.01 to about 1000 or greater International Units (IU)/mL of activity, and more preferably about 100 to about 1000 IU/mL. In yet other embodiments, thrombin may be present in the composition in a concentration of from about 500 to about 1000 IU/mL or greater of activity. In still other embodiments, thrombin may be present in the composition in a concentration of from about 50 to about 500 IU/mL.

The fibrinogen, thrombin, FXIII or other natural protein used in the composition may be substituted by other naturally occurring or synthetic compounds or compositions which fulfill the same functions, such as a reptilase coagulation catalyzed, for example, ancrod, in place of thrombin.

In some embodiments, the hemostatic composition of the present invention will additionally comprise an effective amount of an antifibrinolytic agent to enhance the integrity of the clot as the healing process occurs. A number of antifibrinolytic agents are well known and include aprotinin, C1-esterase inhibitor and ε-amino-n-caproic acid (EACA), for example. EACA is effective at a concentration of from about 5 mg/ml to about 40 mg/ml of the final adhesive composition, more usually from about 20 to about 30 mg/ml. EACA is commercially available as a solution having a concentration of about 250 mg/ml. Conveniently, the commercial solution is diluted with distilled water to provide a solution of the desired concentration.

Other biological factors of interest include EGF, TGF-α, TGF-β, TGF-I and TGF-II, FGF, PDGF, IFN-α, IFN-β, IL-2, IL-3, IL-6, hematopoietic factor, immunoglobulins, insulin, corticosteroids and hormones.

In some embodiments, the composition contains at least one antibiotic. The therapeutic dose levels of a wide variety of antibiotics for use in drug release systems are well known. See for example, Collagen, 1988, Vol. III, Biotechnology; Nimni, (Ed.), CRC Press, Inc., pp. 209-221 and Biomaterials, 1980, Winter et al., (Eds.), John Wiley & Sons, New York, pp. 669-676. Anti-microbial agents are particularly useful for compositions applied to exposed wound repair sites. In some embodiments, anti-microbial agents such as silver are useful.

A biological agent may also include non-protein polymers that act to thicken or gel, by interaction with proteins, by tamponnade, or by other mechanisms. Examples include oxidized cellulose, "Vicryl" and other polyhydroxyacids, chitosan, alginate, polyacrylic acids, pentosan polysulfate, carrageenan, and polyorthoesters (e.g., Alzamer).

A biological agent may be a material that forms a barrier to leakage by mechanical means not directly related to the natural clotting mechanisms, such as a "barrier former". Examples of such agents include oxidized cellulose, ionically or hydrogen-bond crosslinked natural and synthetic polymers including chitin, chitosan, alginate, pectin, carboxymethylcellulose, and poloxamers, such as Pluronic surfactants.

Kits

The invention also includes a kit comprising a hemostatic, collagen-based composition as described herein, and an instructional material which describes, for example, applying the hemostatic composition of the present invention, to the tissue of a subject. The kit may optionally include as separate components a collagen reconstituting solution, a biological agent and/or an applicator for administering the hemostatic composition. The applicator may include a rigid tip for accurately delivering the hemostatic composition to the localized target site. The instruction material may further describe the admixing, handling and administration techniques of any such optional components. In preferred embodiments, the kit includes a delivery device having an orifice or opening with a diameter of at least 1.6 mm through which the composition is capable of flowing.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Initial Fabrication Studies

Multiple formulations for the hemostatic compositions of the present invention were fabricated from collagen starting material. Table 3 below provides a qualitative summary of these formulations and the hemostasis testing results. The primary differentiator between materials relates to characteristics pertaining to the ability to physically handle the material, such as the ability to provide precise, localized placement in an actively bleeding site.

TABLE 3

| Formulation | Stays at application site | Does not stick to gauze | Efficacy in hemostasis (w/o thrombin) |
|---|---|---|---|
| Non-crosslinked microfibrillar collagen suspensions (20-60 mg/mL) | No | No | Poor |
| Non-crosslinked gelatin suspensions (20-60 mg/mL) | No | No | Poor |
| Microfibrillar collagen (20 mg/mL) with enzymatic crosslinker (Transglutaminase) | Yes | No | Mild |
| Microfibrillar collagen (20 mg/mL) with polymerizing agent (alginate) | No | No | Mild |
| Glutaraldehyde crosslinked microfibrillar collagen (90 mg/mL) | Yes | Yes | Moderate |
| Glutaraldehyde crosslinked gelatin (180 mg/mL) | Yes | Yes | Moderate |
| Crosslinked fibrillar collagen | Yes | Yes | Moderate |

Based on these preliminary technical evaluations, it was determined that glutaraldehyde crosslinked collagen formulations are preferable. The percent glutaraldehyde crosslinking affects absorption capacity, swelling properties, and in-vivo material resorption.

A variety of drying methods can be used, such as dry heat, vacuum, forced air, lyophilization, microparticle formation (solvent precipitation), and spray drying, for example. The final material properties may be dependent on the method of drying, particularly the exposure time and temperature. For example, swelling characteristics of the hemostatic composition are dependent not only on the material forming the composition (collagen), but also on the porosity of the composition. Thus, swelling characteristics of the resulting hemostatic composition can be controlled by controlling the porosity of the composition.

Particle formation may be a post-drying process step, or may be incorporated into the drying step, such as for microparticle precipitation or spray drying. Particle size and distribution may affect the absorption capacity and homogeneity of the reconstituted material. As contemplated herein, the hemostatic compositions of the present invention are unique from existing devices in their swelling profiles.

Example 2

Determination of Crosslinking Ratios and Drying Conditions

Crosslinking ratios can be determined based on results such as: number of free amine groups; amount of residual crosslinking agent; properties of the dried material; swelling; solubility and various handling properties, such as ease of reconstituting the material, ease of extruding the material after crosslinking, stickiness to tissue (greater stickiness preferred) and stickiness to gauze (less stickiness preferred).

Initial concentrations of collagen (ranging from about 5% to about 1% solids, or about 50 mg/mL to 10 mg/mL collagen, respectively) for crosslinking were explored in greater detail. Several crosslinking ratios were also explored in greater detail, ranging from 500:1 up to 50:1 and particularly ratios of about 500:1, 250:1 and 100:1. The extent of crosslinking for all materials was determined using a trinitrobenzenesulfonic acid (TNBS) assay. This assay determined the number of free amine groups, in moles, remaining after the crosslinking reaction. This number can be converted into a percent (crosslinking extent) or ratio of non-crosslinked to crosslinked amine groups. Overall the results show that as the crosslinking extent increases the number of free amine groups decreases. At very low crosslinking ratios (500:1) the sensitivity of the assay becomes limited. The results of this test are provided in Table 4, below.

TABLE 4

| | Absorbance (nm) | Free Amine Groups | % Crosslinked |
|---|---|---|---|
| Non-crosslinked | 0.8027 | $1.92 \times 10^{-4}$ | 0 |
| 500:1 | 0.8363 | $1.99 \times 10^{-4}$ | 0 |
| 250:1 | 0.7760 | $1.85 \times 10^{-4}$ | 3.32 |
| 100:1 | 0.6960 | $1.66 \times 10^{-4}$ | 13.1 |

Further, an N-methyl benzothiazolone hydrazone (MBTH) assay allows the amount of residual crosslinking agent, glutaraldehyde (GTA) to be determined. The crosslinked collagen solution was centrifuged, and a sample of the liquid was collected. The crosslinked pellet was resuspended in USP water, and washed with a volume of water equal to that of the water in the initial crosslinking step. This step was repeated, and a total of 3 samples (reaction water, water from rinse 1 and water from rinse 2) were obtained for each crosslinking ratio. With higher crosslinking ratios (above 100:1), low levels of residual GTA were detected in all samples. Materials made at lower crosslinking ratios (250:1 and lower) showed no residual GTA after the second rinse step. The results of this test are provided in Table 5, below.

TABLE 5

| | Absorbance | GTA (ppm) |
|---|---|---|
| 500:1 | 0.052 | 0 |
| 250:1 | 0.054 | 0 |
| 100:1 | 0.089 | $5.89 \times 10^{-4}$ |

Figure 3:
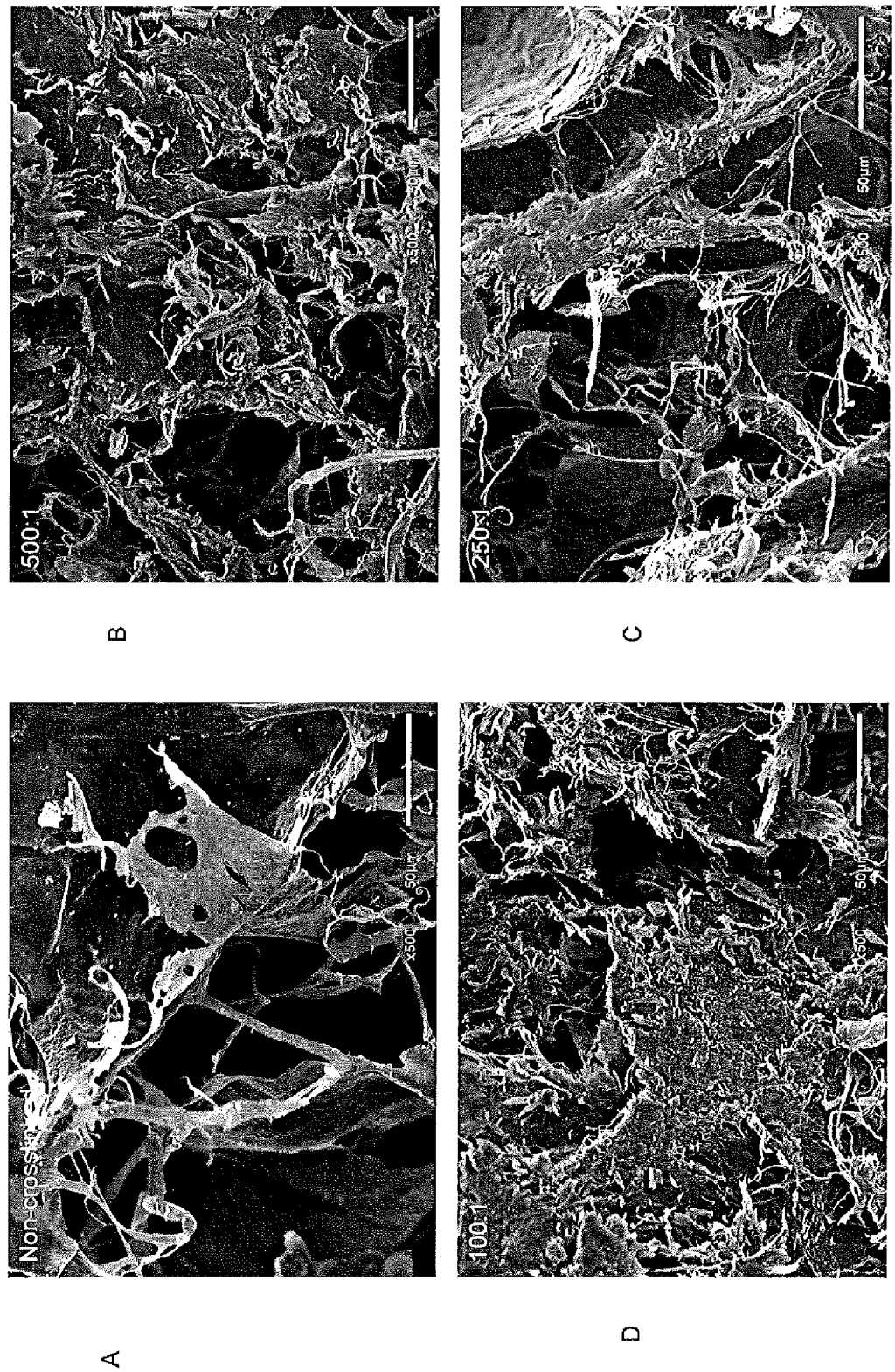
FIG. 3, comprising
Figure 4:
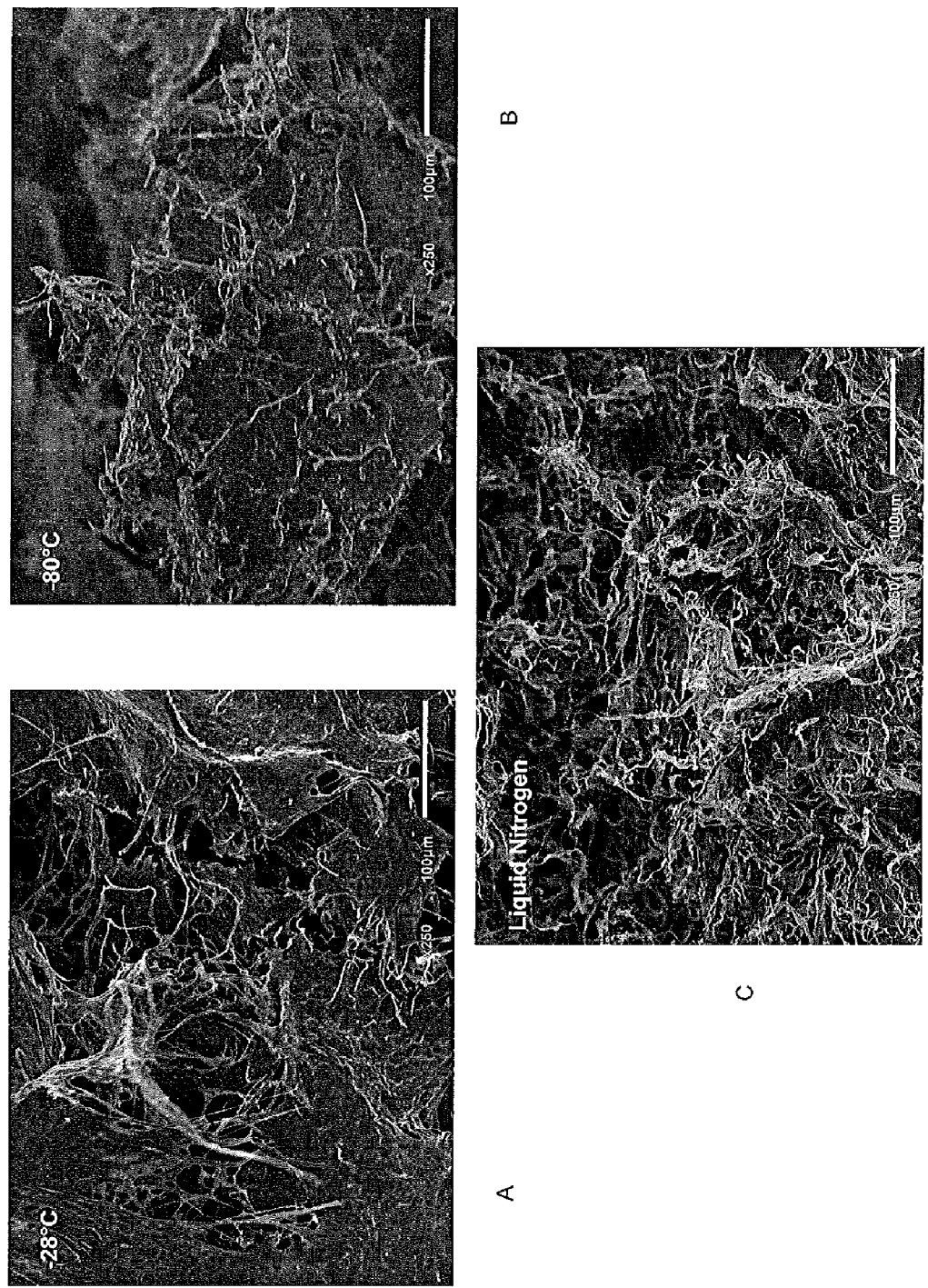
FIG. 4, comprising

After crosslinking and rinsing, the crosslinked collagen pellet was frozen and lyophilized. More specifically, samples were lyophilized for about 2-3 days using a condenser temperature of about −50 to about −60° C. under vacuum. Several freezing temperatures were studied to determine how they affected the material properties. Crosslinked pellets were frozen in liquid nitrogen (about −196° C.) or at about −80 or about −28° C. SEM imaging confirms that freezing temperature affects pore size. As shown in FIGS. 2-4, material frozen in liquid nitrogen has the most open, porous structure and material frozen at the highest temperature, −28° C. has fewer pores and a more "sheet-like" appearance.

The properties of the dried materials were also studied. Materials frozen in liquid nitrogen, regardless of crosslinking ratio, have a larger static charge associated with them as compared to the materials frozen at −80 and −28° C.

The crosslinked materials were also tested for percent swelling, which is an indication of how much additional fluid the material absorbs when placed in a fluid at physiological conditions. To test for percent swelling, crosslinked collagen material was reconstituted to the desired concentration, and then extruded into dialysis tubing. The tubing was incubated in USP water or PBS (phosphate buffered saline) at 37° C. for 24 hours. The increase in mass for each sample was recorded and used to determine the percent swelling, according to the formula:

$$\% \text{ Swelling} = \frac{100 \times (\text{weight after swelling} - \text{weight before swelling})}{\text{weight before swelling}}$$

Preferably, the material should swell sufficiently to absorb blood at the surgical site and facilitate clot formation, preferably between about 0% to about 20% within 10 minutes when reconstituted, and 300-800% for dried material. Further swelling beyond a short time period is undesirable as expansion of material in a surgical site can lead to unwanted impingement of the material on surrounding tissues. The material should preferably reach an equilibrium swell within about 24 hours. The results of this study are provided in Tables 6 and 7 below.

TABLE 6 percent swelling of crosslinked microfibrillar collagen materials ± standard error (in USP water)

| Swelling time point | 1% microfibrillar collagen, 100:1 | 1% microfibrillar collagen, 250:1 | 1% microfibrillar collagen, 500:1 |
|---|---|---|---|
| 10 min | 6.71 ± 1.75 | 8.49 ± 5.62 | 0.93 ± 1.27 |
| 24 hour | 15.54 ± 1.43 | 14.08 ± 6.66 | 9.34 ± 1.82 |

TABLE 7 percent swelling of crosslinked fibrillar collagen materials ± standard error (in PBS)

| Swelling time point | 1% fibrillar collagen, 10:1 |
|---|---|
| 10 min | 4.42 ± 0.43 |
| 24 hour | 2.83 ± 1.11 |

For reference, the Floseal® (Baxter) Instructions For Use document states that the particles of the Floseal® Matrix swell approximately 20% upon contact with blood or other fluids; and that maximum swell volume is achieved within about 10 minutes. And the Surgiflo® (Ethicon) Instructions For Use document states that Surgiflo® may swell approximately 19% upon contact with additional fluid. Other studies conducted on the Floseal® and Surgiflo® competitive products show an average percent swell of about 32% and about 26%, respectively:

To evaluate handling properties, the collagen material was cut into 2.5 cm cubes or ground and the crosslinked collagen was reconstituted at a desired concentration, such as between about 120-160 mg/mL. As the crosslinking ratio increased (e.g., from 500:1 to 250:1 to 100:1), the amount of force required for mixing also increased. While the amount of force required for mixing the various crosslinking ratios was distinct for each sample, the difference in required force for mixing the lowest crosslinking ratios of 500:1 and 250:1 was minimal.

Once reconstituted, the amount of force necessary to extrude the material from a syringe was considered. Syringes contained 4 cc of material reconstituted at 160 mg/mL. The plungers were displaced 0.5" at a rate of 2"/min. The collagen material crosslinked at 100:1 required the greatest extrusion force, while the collagen materials crosslinked at 250:1 and 500:1 required a comparable amount of extrusion force, and significantly less force than the material crosslinked at 100:1. The results of this study are provided in Table 8, below.

TABLE 8

|  | 1% collagen, 100:1 | 1% collagen, 250:1 | 1% collagen, 500:1 |
|---|---|---|---|
| Maximum load, n = 1 (lbf) | 7.53 | 5.06 | 4.91 |
| Maximum load, n = 2 (lbf) | 7.23 | 5.79 | 5.63 |
| Average maximum load (lbf) | 7.38 | 5.43 | 5.27 |

The stickiness of the collagen material to tissue was also evaluated. Preferably, it is desirable that the material remain on the wound (or targeted tissue site) to most effectively stop bleeding. To test this, crosslinked collagen materials were extruded onto a chicken liver ex-vivo and a slow, steady flow of 5 cc of blood was passed over the material. In a second test to determine stickiness to tissue, an incision was made in the liver and blood was slowly dispensed through the "wound site." Material was added on top of the wound site as the blood was being expelled, preferably, the collagen material remains in place, absorbs blood and remains in a generally cohesive mass. All compositions (e.g., 500:1, 250:1, 100:1 of 1% crosslinked microfibrillar collagen and 25:1 and 40:1 of 0.1% and 1% crosslinked fibrillar collagen) performed similarly, showing comparable stickiness to tissue.

The ability of the collagen material to not stick to gauze was also evaluated. To test this, pressure was manually applied to the collagen material using gauze to help pack it into the wound (or targeted tissue site) and stop bleeding. Pressure was released and the gauze carefully removed so as not to disrupt the clot. All materials show similar properties and do not stick to gauze.

Based on these experiments, it was determined that the 1% microfibrillar collagen material having about a 250:1 crosslinking ratio and 0.1% and 1% crosslinked fibrillar collagen having crosslinking ratios of 25:1 and 40:1 were preferable. The factors that influenced this determination were that 500:1 and 250:1 and crosslinked fibrillar collagen were comparable in all handling/extrusion/bleeding tests and assays. Both materials crosslinked at 500:1 and 250:1 as well as some crosslinked fibrillar collagen formulations provided an insoluble crosslinked material, which was also desirable. However, the 250:1 ratio demonstrated an appreciably higher percent crosslinking and it also had no detectable residual GTA after the second rinse.

Example 3

Solubility Testing of Crosslinked Formulations of Microfibrillar Collagen

The solubility of various crosslinked formulations was measured by placing dried, crosslinked and non-crosslinked materials in PBS, incubating under physiologic conditions and measuring for the amount of protein dissolved into the surrounding medium. The following materials were tested: Knox gelatin powder; non-crosslinked microfibrillar collagen (processed as 1% solids); microfibrillar collagen crosslinked at a ratio of 100:1 (processed as 1% solids); microfibrillar collagen crosslinked at a ratio of 250:1 (processed as 1% solids); and microfibrillar collagen crosslinked at a ratio of 500:1 (processed as 1% solids).

One hundred (100) mg of each material was placed in a separate container with 10 mL PBS for 15 minutes at 37° C. No agitation or vortexing was applied. The tubes were then centrifuged and the supernatant was removed and filtered with a 0.22 μm filter to remove any non-solubilized material. The concentration of protein in the collected filtrate was measured using a bicinchoninic acid (BCA) assay kit. The BCA assay is a colorimetric assay that uses copper ions and bicinchoninic acid to react with the peptide bonds in proteins, producing a distinct color change dependent on the amount of protein present. Protein concentrations in this study were compared to a standard curve of bovine albumin protein in PBS. The results of this experiment are presented in Table 9.

TABLE 9

| Measured concentration of soluble protein for various crosslinking ratios of collagen and gelatin. | | | | |
|---|---|---|---|---|
|  | Gelatin powder | 1% solids microfibrillar collagen, crosslinked at a ratio of 500:1 | 1% solids microfibrillar collagen, crosslinked at a ratio of 250:1 | 1% solids microfibrillar collagen, crosslinked at a ratio of 100:1 | Non-crosslinked 1% solids microfibrillar collagen |
| Protein concentration ± SD (μg/mL) | 596.5 ± 8.7 | 0 | 0 | 0 | 31.6 ± 3.9 |

A second experiment was performed to investigate the solubility of various test materials from a reconstituted form, as the reconstituted form is the preferred method of administering the hemostatic composition to the targeted tissue site. The following materials were tested: microfibrillar collagen crosslinked at a ratio of 100:1 (processed as 1% solids), reconstituted at 160 mg/mL; microfibrillar collagen crosslinked at a ratio of 250:1 (processed as 1% solids), reconstituted at 160 mg/mL; microfibrillar collagen crosslinked at a ratio of 500:1 (processed as 1% solids), reconstituted at 160 mg/mL; Floseal® (Baxter), reconstituted according to manufacturer's instructions using 40 μmol CaCl$_2$ solution only (no thrombin); and Surgiflo® (Ethicon), reconstituted according to manufacturer's instructions using saline only (no thrombin).

To approximate adding 100 mg of dried material, 0.625 g of each reconstituted material was added to separate tubes containing 10 mL PBS. All other procedures used were the same as described herein. The results of this experiment are presented in Table 10 below.

TABLE 10

Measured concentration of soluble protein for reconstituted collagen and gelatin materials.

| | 1% solids microfibrillar collagen, crosslinked at a ratio of 500:1 | 1% solids microfibrillar collagen, crosslinked at a ratio of 250:1 | 1% solids microfibrillar collagen, crosslinked at a ratio of 100:1 | Floseal ® | Surgiflo ® |
|---|---|---|---|---|---|
| Protein concentration ± SD (μg/mL) | 0 | 0 | 0 | 133.0 ± 5.3 | 552.5 ± 12.9 |

The values of measured protein concentration from dry material, shown in Table 9, demonstrate that the gelatin powder had a relatively large portion of soluble protein in comparison to the non-crosslinked microfibrillar collagen. Table 8 demonstrates that after reconstitution, both Floseal® and Surgiflo®, which are gelatin based commercial hemostats, also had a relatively large portion of protein that was soluble in PBS. The filtrate from all three crosslinked formulations of the present invention, however, did not have a measurable change in absorbance, in either the dry or reconstituted forms. This confirms that the crosslinked microfibrillar collagen material of the present invention is substantially insoluble in these physiologic conditions.

Example 4

Solubility Testing of Crosslinked Formulations of Fibrillar Collagen

The solubility of various fibrillar collagen crosslinked formulations was also measured by placing dried, crosslinked and non-crosslinked materials in PBS, incubating under physiologic conditions and measuring for the amount of protein dissolved into the surrounding medium. The following materials were tested: 0.1% fibrillar collagen crosslinked at a ratio of 7.5:1; 0.1% fibrillar collagen crosslinked at a ratio of 10:1; 0.1% and 1% fibrillar collagen crosslinked at a ratio of 25:1; 0.1% and 1% fibrillar collagen crosslinked at a ratio of 40:1.

One hundred (100) mg of each material was placed in a separate container with 10 mL PBS for 15 minutes at 37° C. No agitation or vortexing was applied. The tubes were then centrifuged and the supernatant was removed and filtered with a 0.22 μm filter to remove any non-solubilized material. The concentration of protein in the collected filtrate was measured using a bicinchoninic acid (BCA) assay kit. The BCA assay is a colorimetric assay that uses copper ions and bicinchoninic acid to react with the peptide bonds in proteins, producing a distinct color change dependent on the amount of protein present. Protein concentrations in this study were compared to a standard curve of bovine albumin protein in PBS. The results of this experiment are presented in Table 11.

TABLE 11

Measured concentration of soluble protein for various formulations of crosslinked fibrillar collagen.

| Formulation | Protein concentration ± SD (μg/mL) |
|---|---|
| 0.1% fibrillar collagen, 7.5:1 | 0 |
| 0.1% fibrillar collagen, 10:1 | 0 |
| 0.1% fibrillar collagen, 25:1 | 0 to 29.58 ± 4.5 |

TABLE 11-continued

Measured concentration of soluble protein for various formulations of crosslinked fibrillar collagen.

| Formulation | Protein concentration ± SD (μg/mL) |
|---|---|
| 1.0% fibrillar collagen, 25:1 | 4.74 ± 8.2 |
| 0.1% fibrillar collagen, 40:1 | 58.58 ± 6.6 |
| 1.0% fibrillar collagen, 40:1 | 0 |

Example 5

Freezing Temperature Study 1% Collagen Crosslinking Ratio (100:1)

As explained previously, a variety of drying methods can be used, such as dry heat, vacuum, forced air, lyophilization, microparticle formation (solvent precipitation), and spray drying, for example. The final material properties may be dependent on the method of drying, particularly the exposure time and temperature. For example, swelling characteristics of the hemostatic composition are dependent not only on the material forming the composition (collagen), but also on the porosity of the composition and the amount of crosslinking. Thus, swelling characteristics of the resulting hemostatic composition can be controlled by controlling the porosity of the composition. As contemplated herein, the porosity of the composition can be manipulated by the temperature and/or the rate of freezing during the drying process. Porosity can also be manipulated according to the crosslinking ratio used in the crosslinking steps during fabrication. The total porosity of the hemostatic composition is preferably greater than about 50% with interconnected pores. The interconnectivity of the pores facilitates quick fluid uptake and retention via capillary action. In preferred embodiments, the porosity is between 70-90%. Macro, meso and microporosity are also desirable, preferably with the majority of the pores being micro or meso pores. As defined herein, macroporosity is defined by pores having pore diameters greater than about 100 μm, mesoporosity is defined by pores having pore diameters between about 10 μm to 100 μm, and microporosity is defined by pores having pore diameters less than about 10 μm.

As shown in FIG. 3, the porosity of the material and the pore size decreases as the crosslinking ratio increases. Non-crosslinked material has a very open, interconnected pore structure with many collagen fibers visible. In materials crosslinked at 500:1 and 250:1 some fibers can be distinguished, and many pores are still observed, however there is an increase in the sheet-like surfaces present. Whereas the material crosslinked at 100:1 appears more sheet-like.

Freezing temperatures were also studied to help evaluate the structural effects (such as porosity) of the resulting lyophilized collagen materials (or scaffolds). Collagen materials or scaffolds of 1% collagen crosslinked at 100:1 were frozen in liquid nitrogen (10 min), at −28° C. (2-3 hours) and at −80° C. (2-3 hours). Samples were then lyophilized for about 2-3 days using a condenser temperature of about −50 to about −60° C. under vacuum. It was observed that higher freezing temperatures produced larger pore sizes. It was also observed that higher freezing temperatures (e.g., −28° C. and −80° C. compared to a liquid nitrogen temperature of about −196° C.), produced less open structure (more sheet-like with less surface area), whereas the scaffolds frozen in liquid nitrogen had a more open structure (more surface area), and smaller pores. Further, it was observed that the freezing temperature affects the amount of static charge. Particularly, the higher the freezing temperature, the less static charge.

Figure 11:
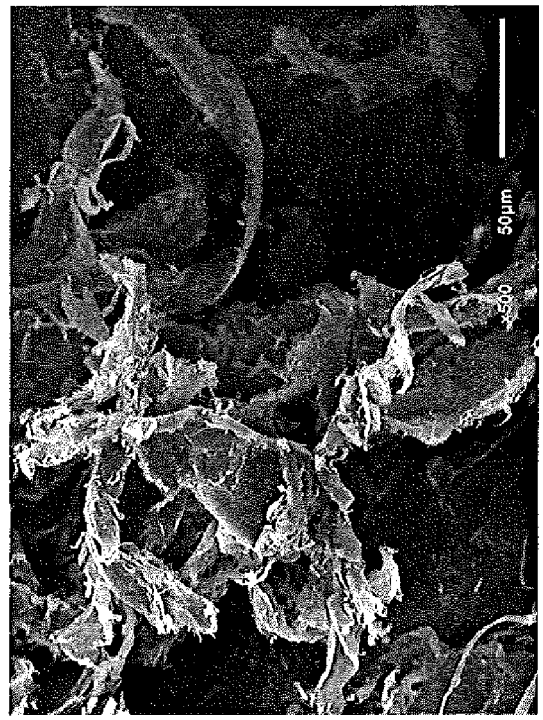
FIG. 11, comprising
Figure 11:
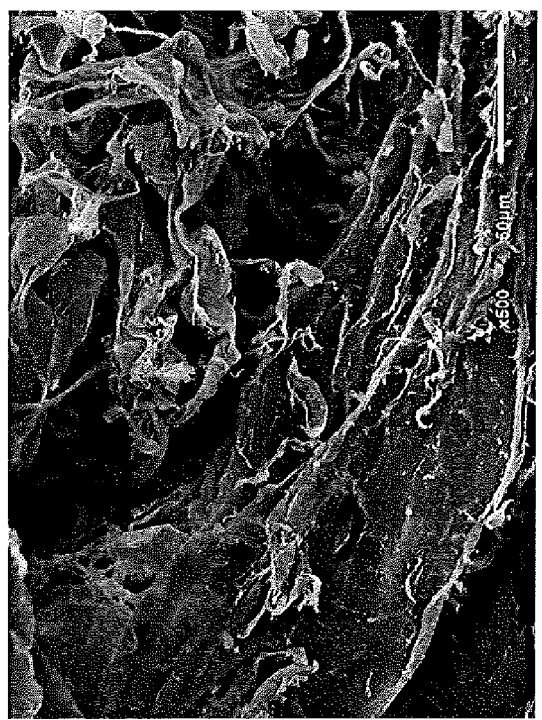
Figure 12:
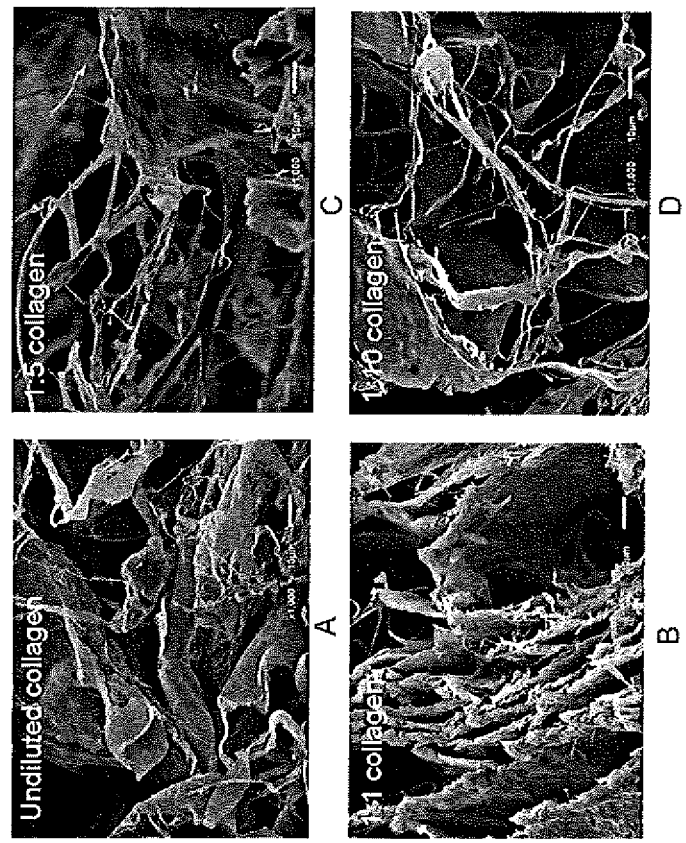
FIG. 12, comprising

In certain embodiments, greater surface area is desirable, as this additional surface area may create a better platform for platelet adhesion and clot stabilization, and establish hemostasis (see Example 6 and FIGS. 10-12, below). In other embodiments aimed at wound healing, less surface area and larger pores may be desirable. Generally, a surface area of between about 0.5 to about 30 $m^2/g$ is preferred.

Figure 5:
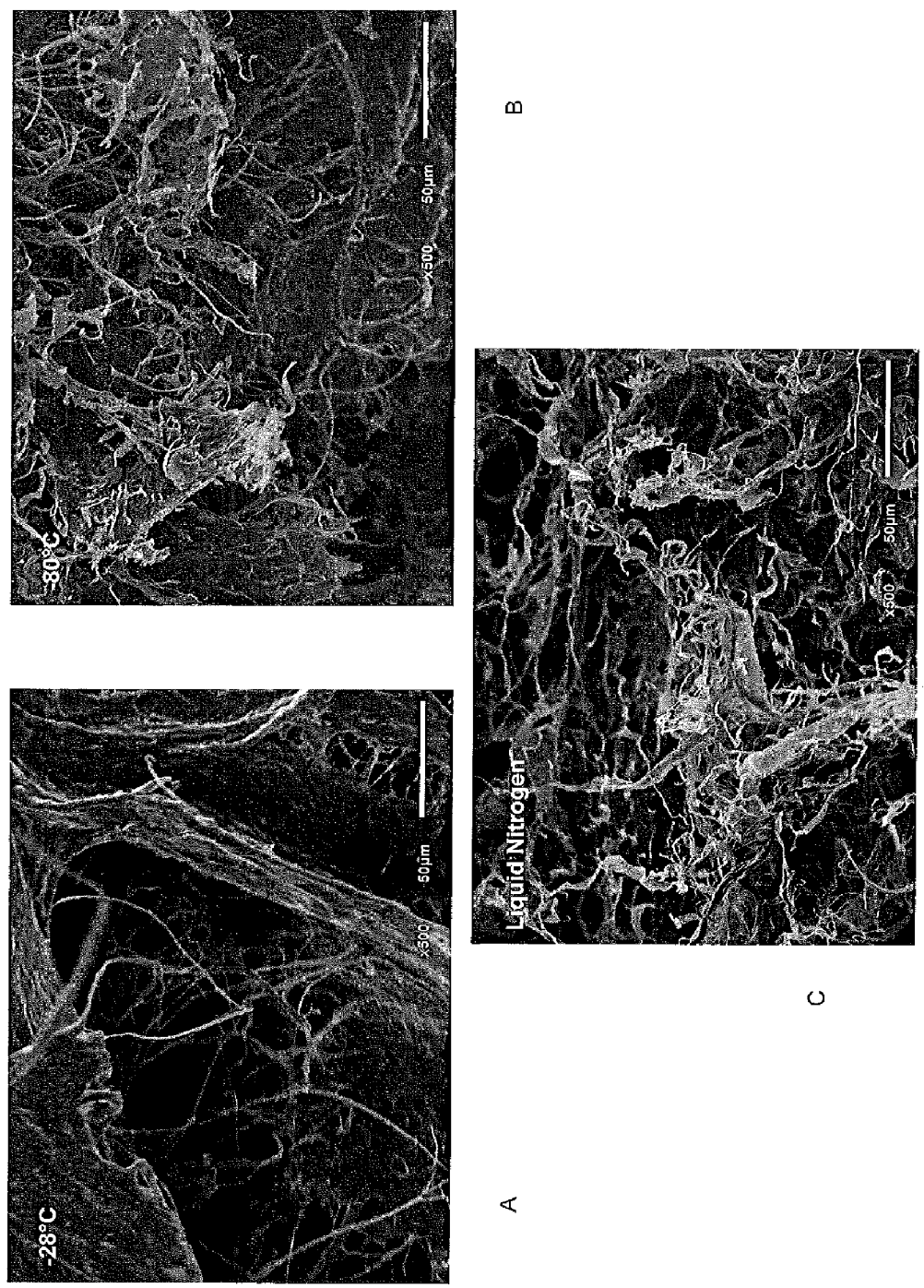
FIG. 5, comprising
Figure 6:
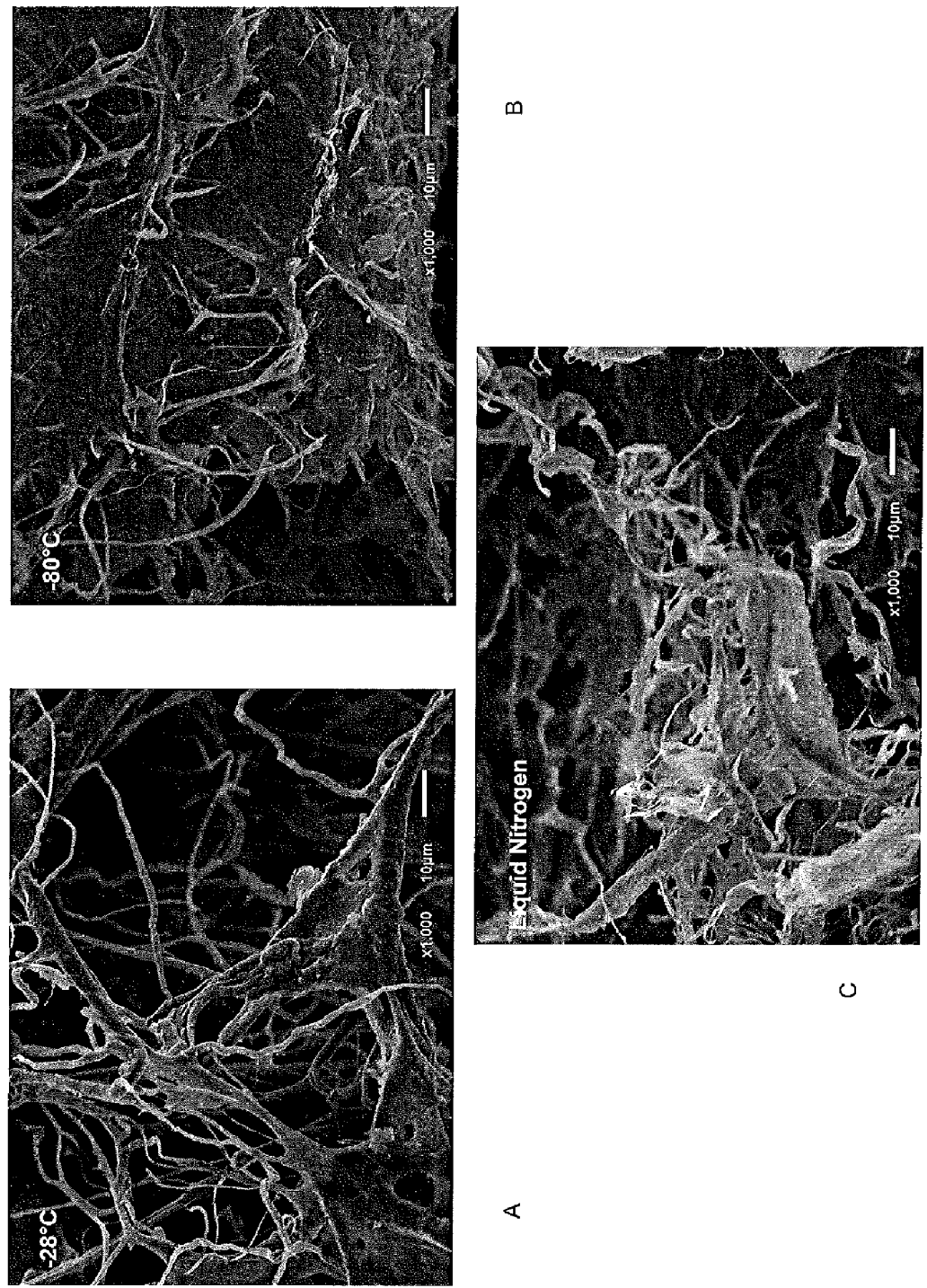
FIG. 6, comprising

As shown in FIGS. 4-6, the scaffolds frozen at −28° C. and −80° C. appear like "sheets" of material, where some pores are observed. However, scaffolds frozen in liquid nitrogen have a more open structure, many small pores, with lots of individual collagen fibers observed. It should be noted that at higher magnifications, fibers can be seen for all freezing conditions.

Freezing temperatures were also studied to help evaluate the physical effects of the collagen material after reconstitution. Collagen materials or scaffolds of 1% collagen crosslinked at 100:1 from samples frozen in liquid nitrogen (10 min), at −28° C. (2-3 hours) and at −80° C. (2-3 hours) were ground using 3×3 sec pulses, and reconstituted in 200 μM $CaCl_2$ at 150 mg/mL of crosslinked material. It was observed that the collagen material frozen in liquid nitrogen was thick, the material frozen at −80° C. was slightly watery, and the material frozen at −28° C. had fluid come out initially, indicating that the material held less fluid and began to phase separate. Regarding the handling properties for each sample, all collagen materials for each sample extruded well, and none of the collagen materials were too sticky to gloves or gauze. All material samples absorbed blood.

Figure 7:
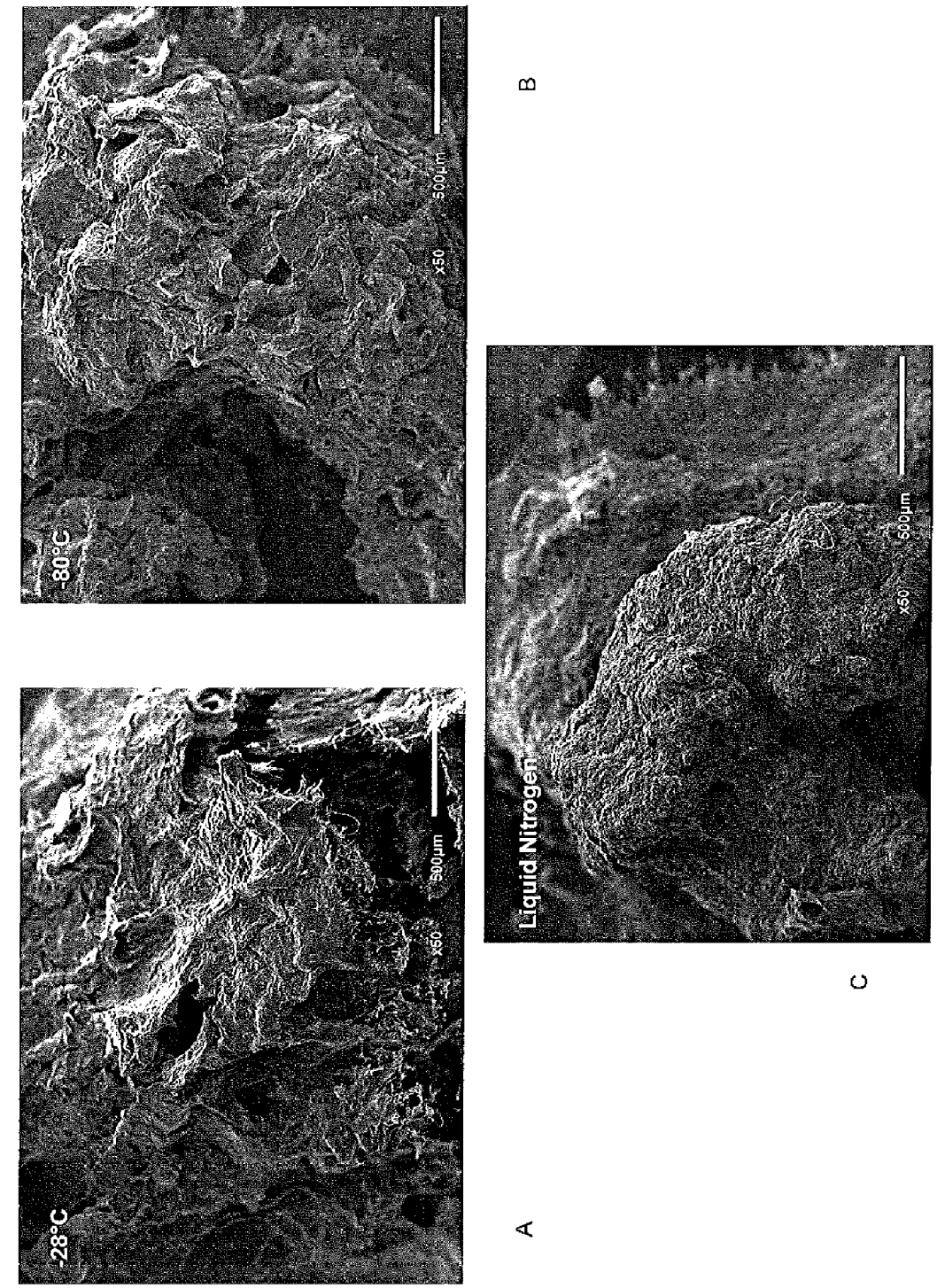
FIG. 7, comprising
Figure 8:
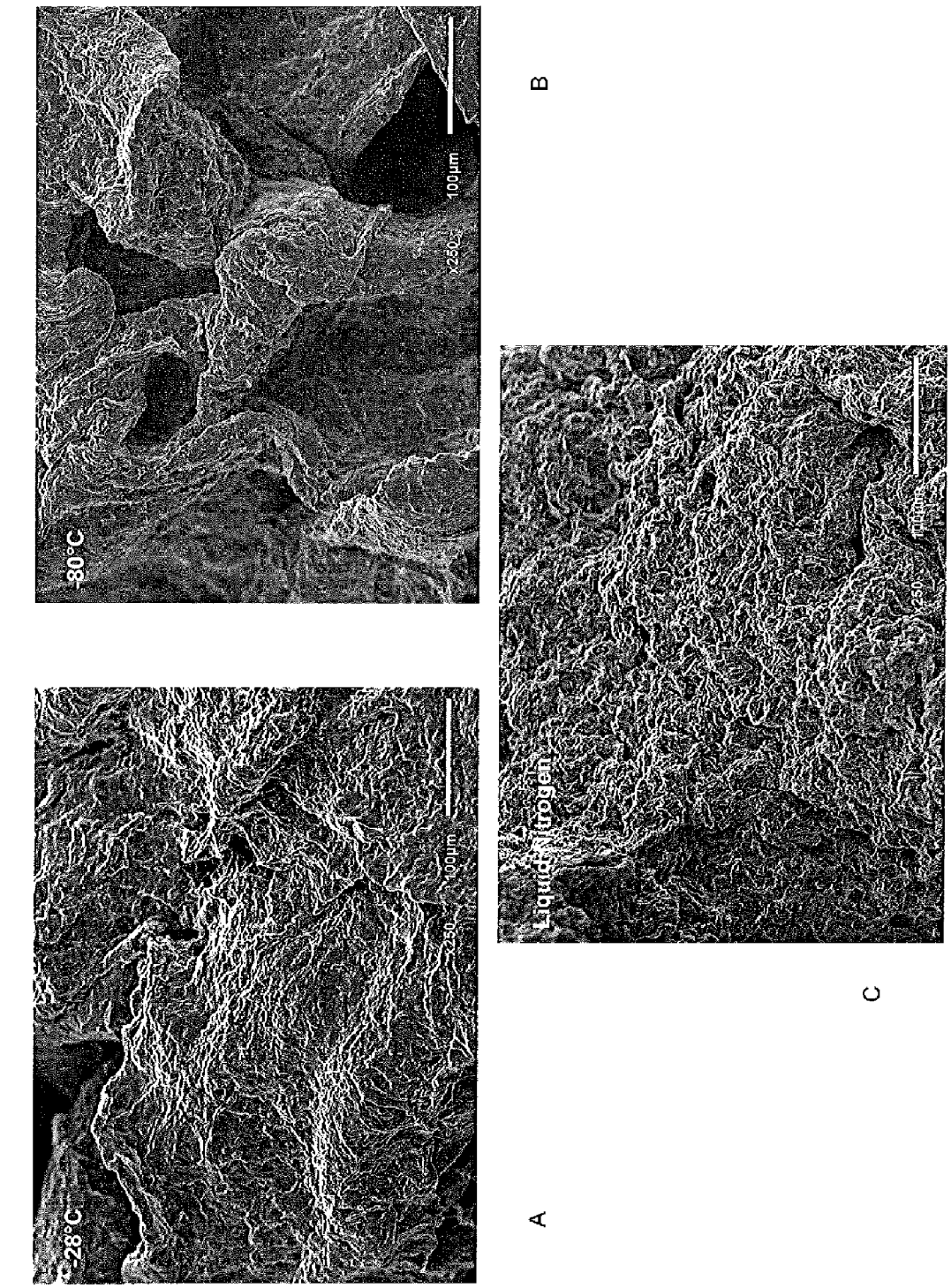
FIG. 8, comprising
Figure 9:
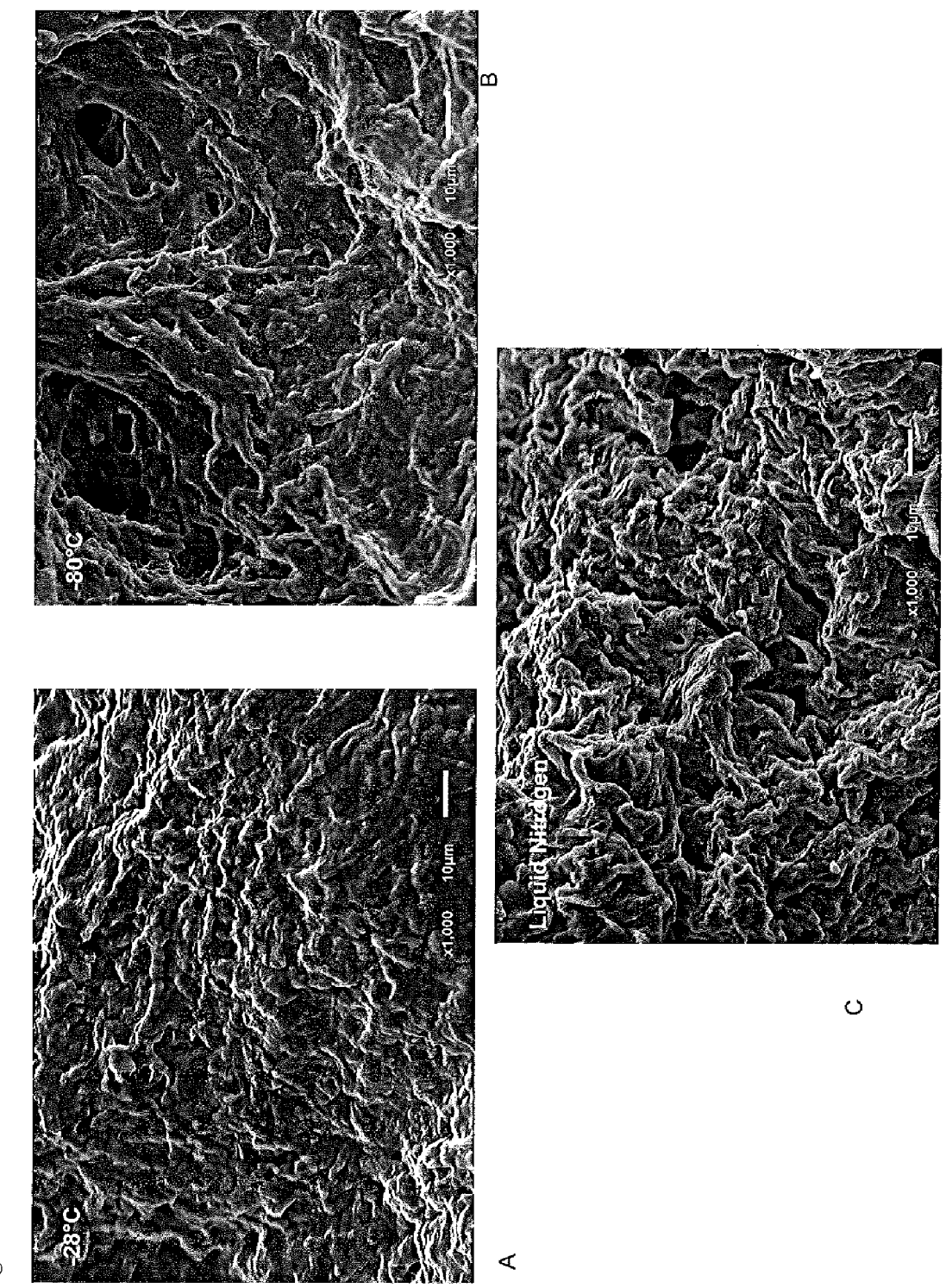
FIG. 9, comprising

As shown in FIGS. 7-9, the surface appearance of the scaffolds frozen at −28° C. and −80° C. appeared like crumpled paper, with smooth surfaces and peaks, and few large pores. The scaffolds frozen in liquid nitrogen appeared to have a smoother and flatter surface, with no peaks and valleys. At higher magnifications, fibers were observed. Notably, the collagen materials, regardless of freezing conditions, were more similar after reconstitution, in that there was less open space and the materials are more of a cohesive mass. However, it was observed that the thickness of the collagen material reconstituted at the same concentration increases with decreasing freezing temperature. This suggests that the absorption capacity of a given material is higher when lower freezing temperatures are used.

From this, it appears that the rate of drying can help control pore size and material thickness, resulting in the ability to optimize and/or select for the properties of the resulting hemostatic composition related to these features.

Example 6

Freezing Rate for Lyophilizing Material

As explained in previous examples, the final material properties may be dependent on the freezing rate of the material, particularly morphology due to crystal formation during the lyophilization process. Approximately forty (40) grams of 1% microfibrillar collagen was crosslinked in glutaraldehyde at a ratio of 250:1 for 4 hours. The collagen was centrifuged at 10,000 RPM for 8 minutes. The material was rinsed twice with additional centrifugation between each rinse. The pellet was then spread evenly in a reservoir, between a 2-3 mm thickness, for lyophilization. The samples were frozen at −50° C. for 4-5 hours, then subjected to a programmed lyophilization cycle run for a duration of approximately 30 hours. Samples lyophilized using a first freezing rate (−1° C./min) had mostly sheets with slight fraying. Samples lyophilized using a slower freezing rate (−0.5° C./min) had more ribbon-like materials with moderate fraying, as shown in the SEM images below. Collagen materials were ground and reconstituted in saline at 150 mg/mL of crosslinked material. As listed in Table 12, blood absorption was 27.88% for the faster freezing rate and 15.28% for the slower freezing rate as summarized in the table below. The results from this experiment demonstrate that the rate of freezing rate can affect both the morphology and the ability of the material to absorb blood. As seen in FIGS. 11A and 11B, the faster freezing rate resulted in more sheet-like materials compared to the slower freezing rate which resulted in ribbons.

TABLE 12

Blood absorption of collagen materials lyophilized using two different freezing rates

| Formulation Description | Average Blood absorption (%) ± SD |
| --- | --- |
| Glutaraldehyde crosslinked microfibrillar collagen. 250:1 @ a freezing rate of −1° C./min | 27.88 |
| Glutaraldehyde crosslinked microfibrillar collagen. 250:1 @ a freezing rate of −0.5° C./min | 15.28 |

Example 7

Blood Absorption of Hemostatic Materials

The ability of various crosslinked formulations to absorb blood was investigated by partially submerging (~40%) the reconstituted materials in porcine blood for 2 minutes. The mass of each material was measured before and after placement in blood and used to determine % absorption by mass, according to the formula:

$$\% \text{ Blood Absorption} = \frac{\text{Hydrated mass} - \text{initial mass of material}}{\text{initial mass of material}} \times 100$$

The results from the experiment are summarized in Table 13, below.

TABLE 13

Blood absorption of various formulations of collagen materials.

| Description | Average Blood absorption (%) ± SD |
|---|---|
| Baxter Floseal ®: Reconstituted according to Instructions For Use | 38.24 ± 1.87 |
| 1% microfibrillar collagen, GTA crosslinked at a ratio of 250:1 @ a freezing rate of −1° C./min, non-sterilized | 27.88 (n = 1) |
| 0.1% fibrillar collagen GTA crosslinked at a ratio of 40:1, gamma sterilization | 0.12 (n = 1) |

From these experimental results, it was determined that the gelatin material had the highest absorption followed by microfibrillar collagen and then fibrillar collagen. Overall, the glutaraldehyde crosslinked microfibrillar collagen had higher blood absorption properties compared to fibrillar crosslinked collagen materials. This suggests that blood absorption can be affected by both the crosslinking agent and raw material.

Example 8

Starting Concentration of Material for Lyophilization

The starting concentrations of the material undergoing lyophilization were also studied to evaluate the effects on the structure of the resulting lyophilized collagen materials (or scaffolds). The water content of the starting material has a direct effect on crystal formation during the freezing portion of the lyophilization cycle. Forty (40) grams of 1% microfibrillar collagen crosslinked in glutaraldehyde at a ratio of 250:1 for 4 hours (undiluted collagen material) and diluted collagen materials (1:1; 1:5; 1:10 by volume in USP water for a total of 10 mL for each sample) were frozen at −50° C. for 4-5 hours and then were subjected to a programmed lyophilization cycle run for a duration of approximately 30 hours. As shown in FIGS. 12A-12D, SEM images reveal that starting materials with higher volumes of water had larger pore sizes and more open structures. There was a trend of increasing pore size with more diluted samples as again depicted in FIGS. 12A-12D.

Example 9

Quantification of Surface Area

Surface area analysis was performed using the BET (Brunauer, Emmet, and Teller) theory to calculate the surface area of a sample of 1% microfibrillar collagen crosslinked at a ratio of 250:1. Briefly, approximately 4 g of sample was prepared by degassing overnight to remove impurities. The sample was then cooled with liquid nitrogen and analyzed by measuring the volume of krypton gas adsorbed at specific pressures. The amount of adsorbed gas was used to calculate the total surface area of the material by a multi-point method. Results show a surface area of approximately 0.7809±0.0040 $m^2/g$.

Based on these results, further surface area testing was performed using the BET theory. The following materials were tested: 1% microfibrillar collagen crosslinked at a ratio of 250:1; 1% fibrillar collagen crosslinked at a ratio of 25:1; 0.1% fibrillar collagen crosslinked at a ratio of 40:1; and 1.0% fibrillar collagen crosslinked at a ratio of 40:1. Briefly, approximately 0.1-0.5 g of each ground sample was prepared by degassing overnight to remove impurities. The samples were then cooled with liquid nitrogen and analyzed by the volume of nitrogen gas adsorbed as specific pressures. The amount of adsorbed gas was used to calculate the total surface area of the material by a multi-point method. Results are shown in Table 14.

TABLE 14

Measured surface area of glutaraldehyde crosslinked collagen formulations.

| Sample Type | Surface area ($m^2/g$) ± standard deviation |
|---|---|
| 1% microfibrillar collagen, crosslinked at a ratio of 250:1 | 1.9674 ± 0.0418 |
| 1% fibrillar collagen, crosslinked at a ratio of 25:1 | 0.4180 ± 0.0258 |
| 0.1% fibrillar collagen, crosslinked at a ratio of 40:1 | 2.1472 ± 0.0421 |
| 1.0% fibrillar collagen, crosslinked at a ratio of 40:1 | 2.4881 ± 0.0478 |

Within each formulation type, samples exhibiting a higher surface area tended to have better handling properties such as ease of mixing and material consistency. The investigation of freezing temperatures demonstrates that materials frozen at the lowest temperatures have a more open structure with many small pores and fibers. The surface area results suggest that an increased surface area, such as that visually observed in the freezing temperature study, may contribute to a material's absorption capacity.

Example 10

Hemostasis Testing

A porcine bleeding model was used to assess the hemostatic abilities of various crosslinked formulations. The following materials were tested: 1% collagen crosslinked at a ratio of 100:1; 5% collagen crosslinked at a ratio of 500:1; Floseal®; and Surgiflo®. Crosslinked collagen materials were prepared by grinding lyophilized scaffolds and reconstituting with saline to a concentration of between 120 to 140 mg/mL. Commercial gelatin products were prepared according to the manufacturer's instructions. For collagen test materials of the present invention prepared with thrombin, material was reconstituted using thrombin with a concentration of 1000 IU/mL. For the competitive product materials, the manufacturer's instructions were followed. The concentration of thrombin for Floseal® was 500 IU/mL. The concentration of thrombin for Surgiflo® was 320-480 IU/mL (based on using 2 mL of 800-1200 IU/mL thrombin per the manufacturer's instructions). A 6 mm biopsy punch was used to create a defect approximately 7 mm deep in the kidney, liver, or spleen. The resulting tissue flap was removed using either scissors or a scalpel. Test material was applied to the bleeding site and pressure was held using gauze for 60 seconds. The wound was then observed for bleeding. If hemostasis had not been achieved, additional material was applied and/or pressure was held for another 30 seconds. This was repeated until no bleeding could be observed. Time from material application to hemostasis was recorded. The results of the experiment are presented in Table 15.

TABLE 15

Time to hemostasis for crosslinked collagen materials and commercial gelatin hemostats in a non-heparinized bleeding model.

| Sample Type | Average Time to Hemostasis (seconds) ± standard error |
|---|---|
| 1% microfibrillar collagen, crosslinked at a ratio of 100:1 with 1000 IU/mL thrombin | 89 ± 36 |
| 1% microfibrillar collagen, crosslinked at a ratio of 100:1 | 157 ± 87 |
| 5% microfibrillar collagen, crosslinked at a ratio of 500:1 with 1000 IU/mL thrombin | 78 ± 34 |
| 5% microfibrillar collagen, crosslinked at a ratio of 500:1 | 52 ± 15 |
| Floseal ® | 170 ± 70 |
| Surgiflo ® | 121 ± 45 |

Figure 13:
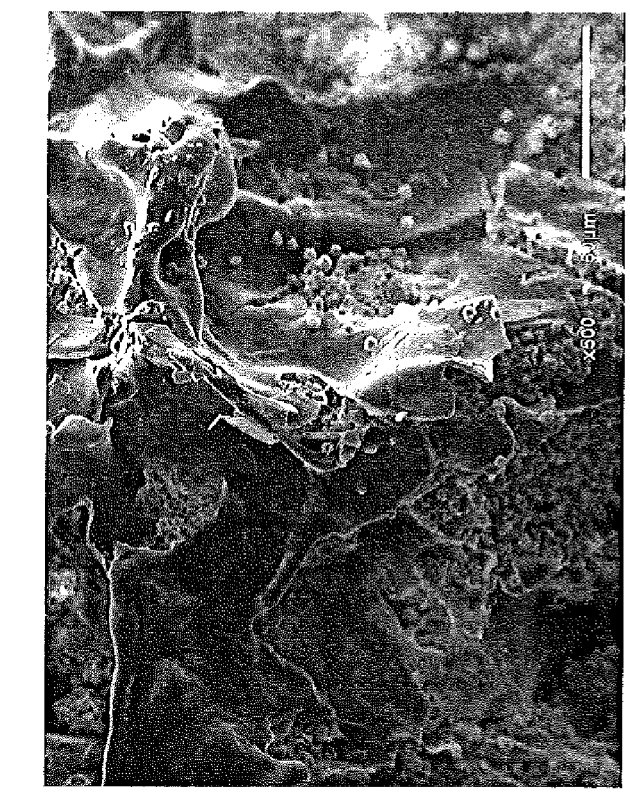
FIG. 13, comprising
Figure 13:
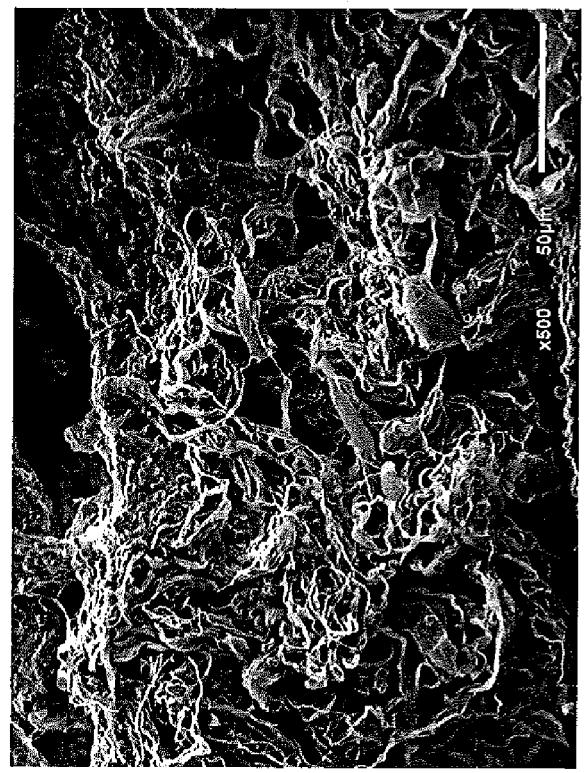
Figure 14:
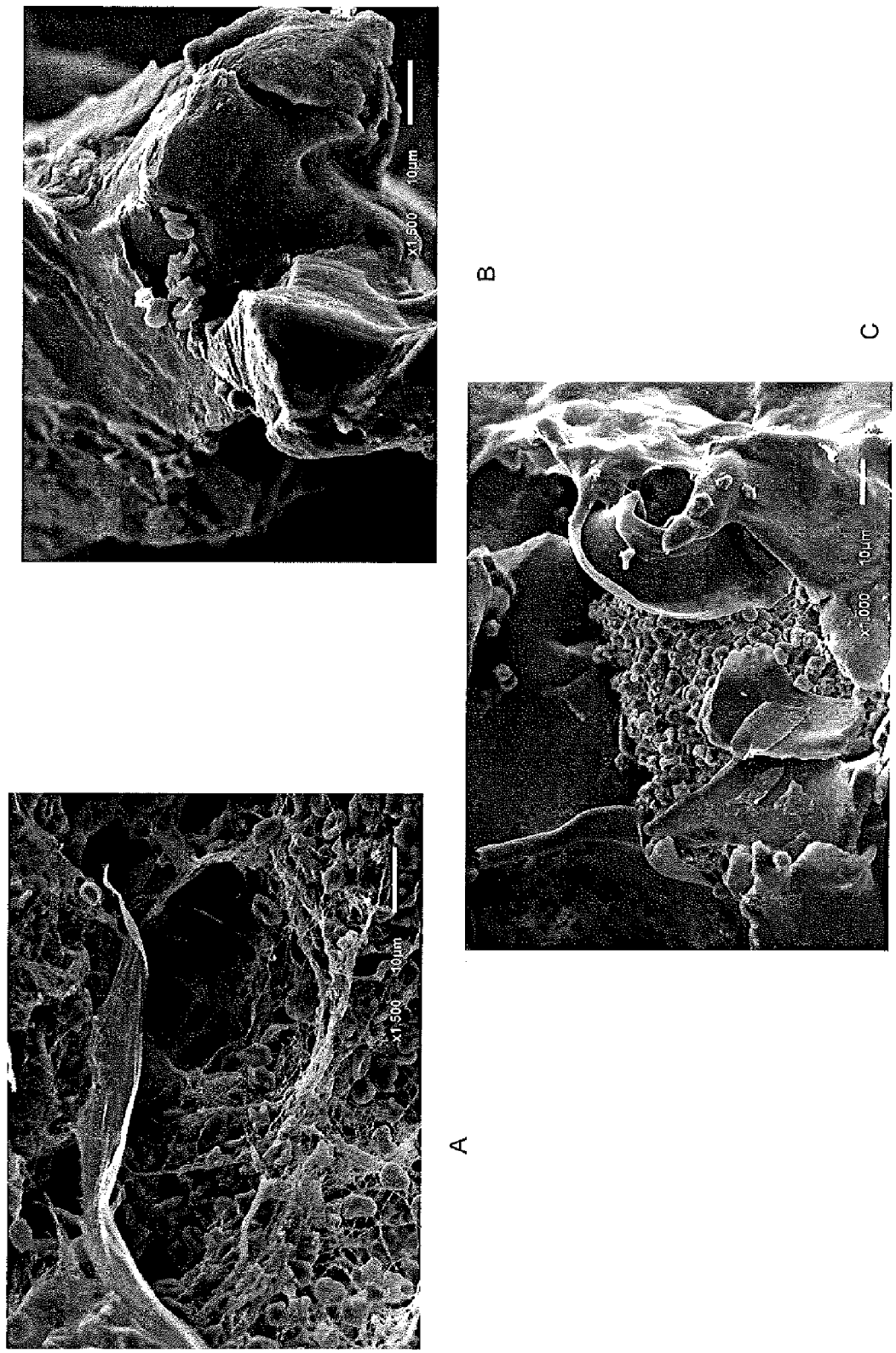
FIG. 14, comprising
Figure 15:
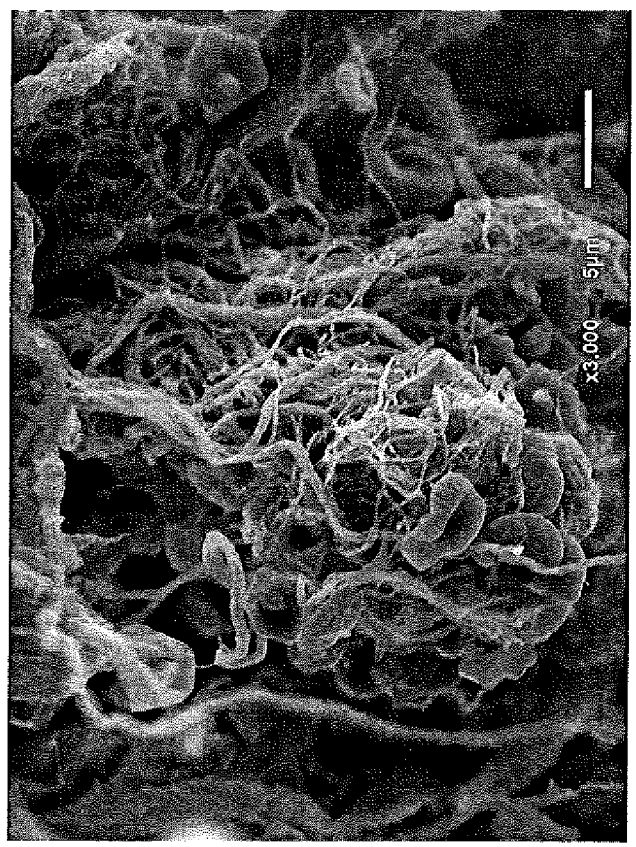
FIG. 15, comprising
Figure 15:

These results can also be seen in FIGS. 13-15. For example, FIGS. 13A-13B are SEM images at a magnification of 500× of 1% collagen (FIG. 13A) and Surgiflo® (FIG. 13B) after hemostasis had been achieved through application of the material to a bleeding site. FIGS. 14A-14C are SEM images of 5% collagen (FIG. 14A, 1500×), Floseal® (FIG. 14B, 1500×), and Surgiflo® (FIG. 14C, 1000×) after hemostasis had been achieved through application of the material to a bleeding site. FIGS. 15A-15B are SEM images at a magnification of 3000× of 1% collagen (FIG. 15A) and 5% collagen without the addition of thrombin (FIG. 15B) after hemostasis had been achieved through application of the material to a bleeding site. In a second set of tests, a porcine bleeding model was used to assess the hemostatic abilities of various crosslinked formulations. The following materials crosslinked with glutaraldehyde were tested: 1% microfibrillar collagen crosslinked at a ratio of 100:1; 1% microfibrillar collagen crosslinked at a ratio of 250:1; 0.1% fibrillar collagen crosslinked at a ratio of 10:1; 0.1% fibrillar crosslinked at a ratio of 25:1; Surgiflo®; and Floseal®. Crosslinked collagen materials were prepared by grinding lyophilized scaffolds and reconstituting with saline to a concentration of 120 to 140 mg/mL. Commercial products were prepared according to the manufacturer's instructions. The concentration of thrombin for Floseal® was 500 IU/mL. The concentration of thrombin for Surgiflo® was 320 to 480 IU/mL (based on using 2 mL of 800-1200 IU/mL thrombin per the manufacturer's instructions). A 6 mm biopsy punch was used to create a defect approximately 7 mm deep in the kidney, liver, or spleen. The resulting tissue flap was removed using scissors or a scalpel. Test material was applied to the bleeding site and pressure was held using gauze for 60 seconds. The wound was then observed for bleeding. If hemostasis had not been achieved, additional material was applied and/or pressure was held for another 30 seconds. This was repeated until no bleeding could be observed. Time from material application to hemostasis was recorded. The results of the experiment are presented in Table 16.

TABLE 16

Time to hemostasis for crosslinked collagen materials and commercial gelatin hemostats in a non-heparinized bleeding model.

| Sample Type | Average Time to Hemostasis (seconds) ± standard error |
|---|---|
| 1% microfibrillar collagen, crosslinked at a ratio of 100:1 | 143 ± 37 |
| 1% microfibrillar collagen, crosslinked at a ratio of 250:1* | 77 ± 17 |
| 0.1% fibrillar collagen, crosslinked at a ratio of 10:1 | 102 ± 15 |
| 0.1% fibrillar collagen, crosslinked at a ratio of 25:1 | 127 ± 15 |
| Surgiflo ® | 78 ± 18 |
| Floseal ® | 60 ± 0 |

*1/4 sites did not achieve hemostasis within 10 minutes.

In a third set of tests, a porcine bleeding model was used to assess the hemostatic abilities of various crosslinked formulations. The following materials were tested: 0.1% fibrillar collagen crosslinked with glutaraldehyde at a ratio of 40:1; 1% fibrillar collagen crosslinked with glutaraldehyde at a ratio of 25:1; crosslinked fibrillar collagen; and Floseal®. Crosslinked collagen materials were prepared by grinding lyophilized scaffolds and reconstituting with saline to a concentration of 120 to 130 mg/mL. Commercial products were prepared according to the manufacturer's instructions. The concentration of thrombin for Floseal® was 500 IU/mL. The concentration of thrombin for Surgiflo® was 320 to 480 IU/mL (based on using 2 mL of 800-1200 IU/mL thrombin per the manufacturer's instructions). A 6 mm biopsy punch was used to create a defect approximately 7 mm deep in the kidney, liver, or spleen. The resulting tissue flap was removed using scissors or a scalpel. Test material was applied to the bleeding site and pressure was held using gauze for 60 seconds. The wound was then observed for bleeding. If hemostasis had not been achieved, additional material was applied and/or pressure was held for another 30 seconds. This was repeated until no bleeding could be observed. Time from material application to hemostasis was recorded. The results of the experiment are presented in Table 17.

The same model was also performed in heparinized animals. The following materials were tested: crosslinked fibrillar collagen; 1% fibrillar collagen crosslinked with glutaraldehyde at a ratio of 25:1; and Floseal®. The concentration of thrombin for Floseal® was 500 IU/mL. The results are presented in Table 18.

TABLE 17

Time to hemostasis for crosslinked collagen materials and commercial gelatin hemostats in a non-heparinized bleeding model.

| Sample Type | Average Time to Hemostasis (seconds) ± standard error |
|---|---|
| 0.1% fibrillar collagen, crosslinked at a ratio of 40:1 | 194 ± 33 |
| 1% fibrillar collagen, crosslinked at a ratio of 25:1* | 211 ± 44 |
| 1% microfibrillar collagen, crosslinked at a ratio of 250:1 | 122 ± 24 |
| Floseal ® | 126 ± 27 |

*1/10 sites did not achieve hemostasis within 10 minutes.

TABLE 18

Time to hemostasis for crosslinked collagen
materials and commercial gelatin hemostats
in a heparinized bleeding model.

| Sample Type | Average Time to Hemostasis (seconds) ± standard error |
|---|---|
| 1% fibrillar collagen, crosslinked at a ratio of 25:1* | 166 ± 70 |
| Floseal ®* | 143 ± 83 |

*⅕ sites did not achieve hemostasis within 10 minutes.

Figure 16:
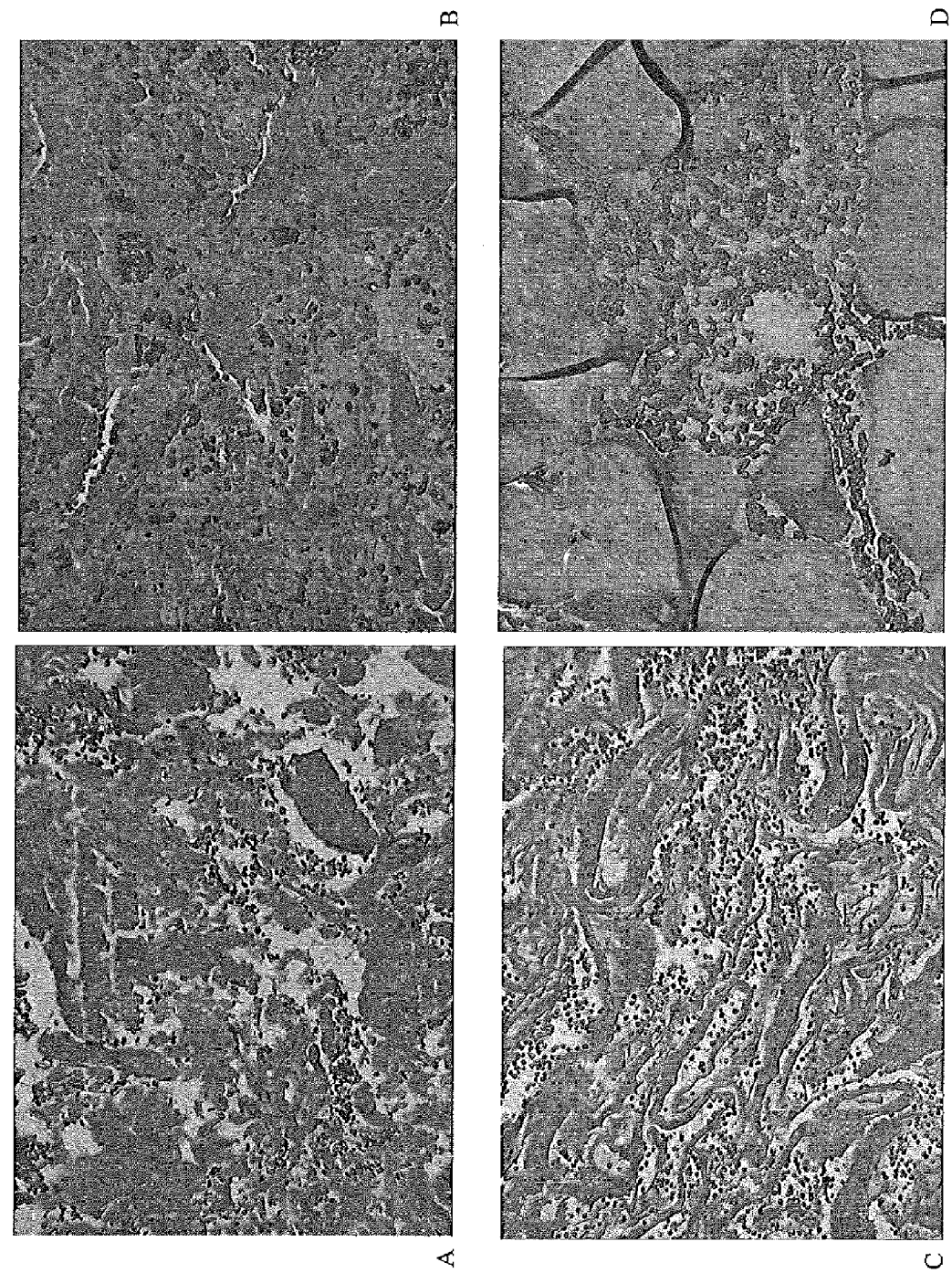
FIG. 16, comprising

Representative histology images of each material following application to a bleeding liver defect are shown in FIG. 16. The fibrillar collagen has a disorganized appearance with red blood cells trapped between pieces of collagen (FIGS. 16A and 16B). The microfibrillar collagen has a more ordered configuration with red blood cells trapped between collagen fibers (FIG. 16C). Floseal® can be observed as large granules of gelatin particles with red blood cells in the interstitial spaces between material particles (FIG. 16D).

Example 11

In Vivo Biocompatibility and Degradation Testing

Figure 17:
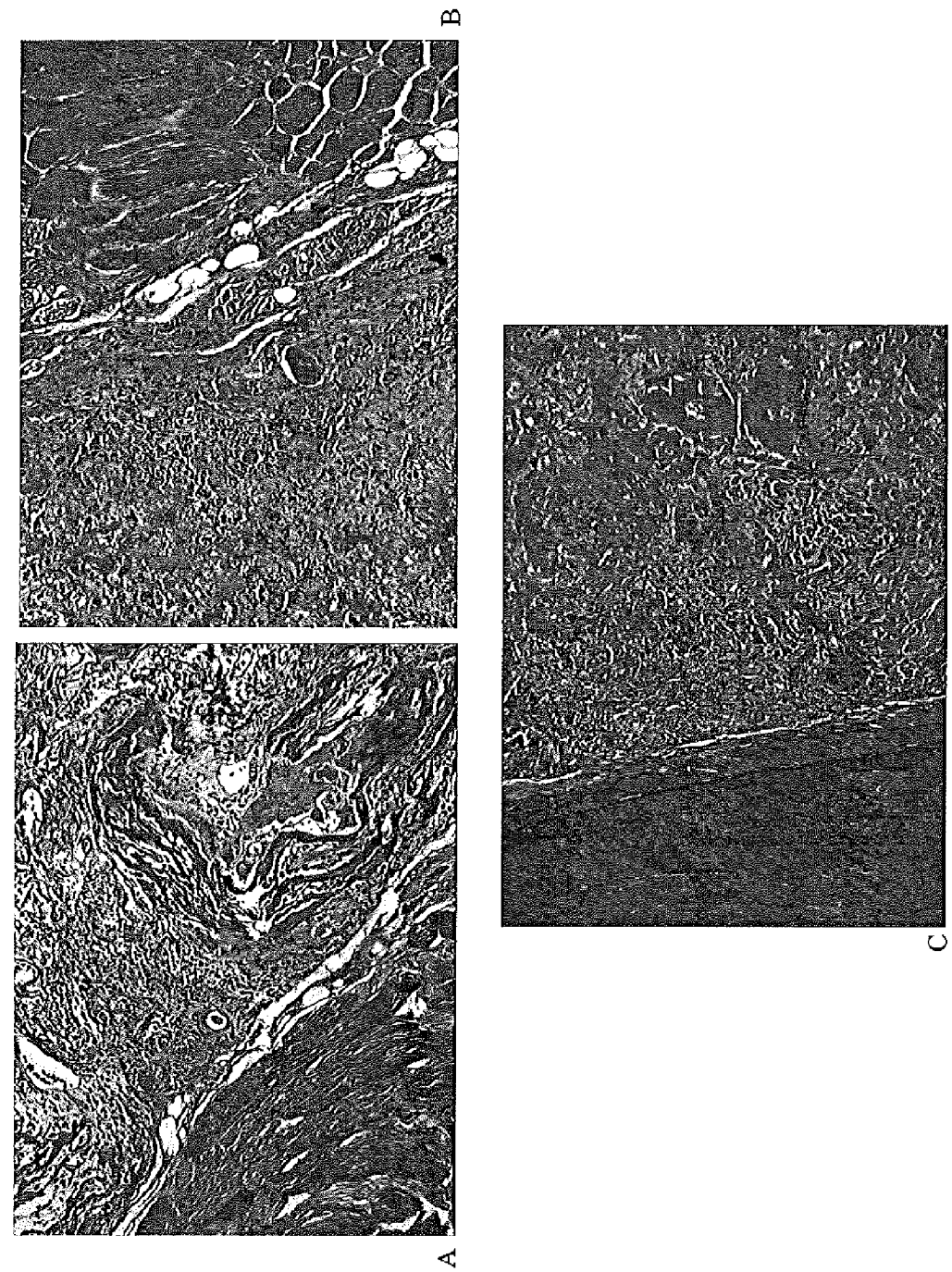
FIG. 17, comprising

A rabbit degradation model was used to assess tissue biocompatibility and in vivo degradation of various crosslinked formulations. The following materials crosslinked with glutaraldehyde were tested: 1% microfibrillar collagen crosslinked at a ratio of 100:1; 1% microfibrillar collagen crosslinked at a ratio of 250:1; and 0.1% fibrillar collagen crosslinked with glutaraldehyde at a ratio of 10:1. Crosslinked collagen materials were prepared by grinding lyophilized scaffolds and reconstituting with saline to a concentration of 110 to 160 mg/mL. An incision was created in the paraspinal muscle and blunt dissection was used to create an intramuscular pocket. Into each pocket, approximately 1 cc of each crosslinked collagen formulation was applied. At 8 weeks, sites were excised and placed en bloc in fixative solution. The tissue samples were processed using standard histological techniques and sections were stained with hematoxylin & eosin and Masson's trichrome. All sites displayed normal healing at necropsy. The amount of material present and appearance of the tissue and implanted collagen material are described in Table 19. Representative histology images are shown in FIG. 17.

TABLE 19

Microscopic analysis of crosslinked collagen materials
at 8 week implantation time.

| Sample Type | Amount of Material Present | Appearance of tissue/material |
|---|---|---|
| 1% microfibrillar collagen, 100:1 | Minimal to marked | Cellular and tissue infiltration, organized muscle tissue formation |
| 1% microfibrillar collagen, 250:1 | Minimal to moderate | Large degree of cellular infiltration, redevelopment of muscle tissue |
| 0.1% fibrillar collagen, 10:1 | Marked | Cellular infiltration only on the outside of material |

Example 12

Determining Crosslinking Conditions Using EDC/NHS Chemistry

Crosslinking can be used to tailor properties of the crosslinked material such as handling properties, blood absorption, material consistency, ability to hold shape, and flexibility. The most preferred material will be able to hold its shape and be extruded through a syringe.

Figure 18:
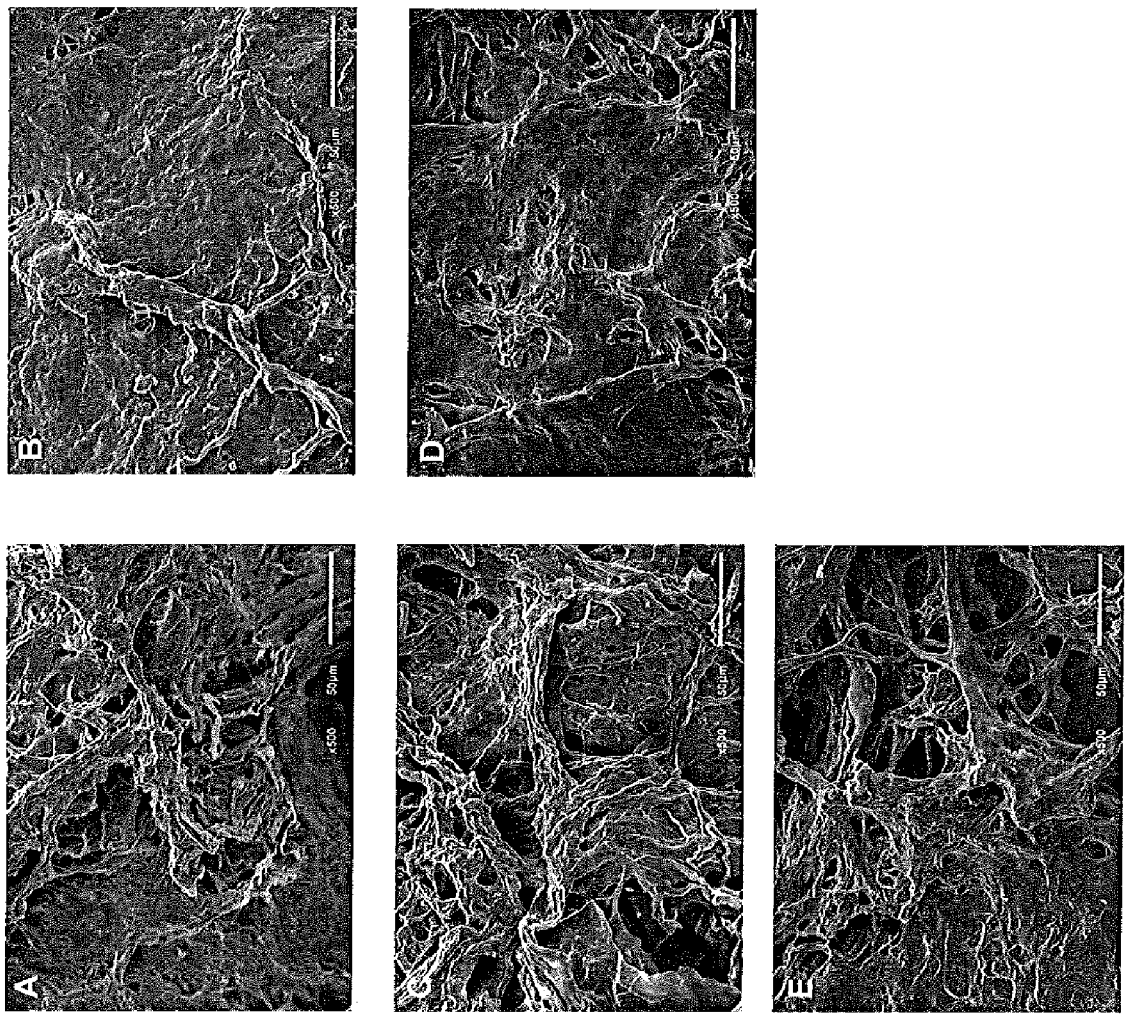
FIG. 18, comprising

In order to crosslink collagen using EDC/NHS chemistry, the general procedure of Wissink (2000) was modified as follows. The concentration of collagen used was between 4-5 mg/mL (0.4-0.5%) and more preferably between 0.45-0.47%. The effect of reaction conditions on material properties were explored in greater detail. Collagen was crosslinked using 1.740 g EDC per 1 g of collagen and 0.42 g NHS per 1 g of collagen. The solution was allowed to stir at room temperature for 4 hours. The mass to mass ratio of EDC to NHS was always kept between 4.0:1 and 4.5:1. The resultant material properties were analyzed using SEM for fiber size and connectivity (See FIG. 18), Fourier-Transform infrared spectroscopy (FTIR) to determine if changes in chemical structure could be observed after crosslinking, blood absorption, and differential scanning calorimetry (DSC) to determine if the stability of the material increased as a result of crosslinking.

The structure of the material is altered as reaction conditions such as concentration and time are varied (See Table 21, below). The control material is shown in FIG. 18A. All materials are compared to this material. Materials crosslinked at lower concentrations; such as about half the concentration of EDC and NHS relative to the control (FIG. 18B) or materials crosslinked for a shorter time, such as about two hours (FIG. 18D), have a more closed, less porous structure. These materials have mostly a sheet-like appearance with a few fibers that are visible. Materials crosslinked at a higher concentration, for example about two times more EDC and NHS were used compared to the control material (FIG. 18C). The increase in concentration appears to result in a more interconnected porous structure with small sheets of material. The reaction time can be increased from about 4 hours for the control material to about 16 hours to provide material that has a more open and porous structure with a few sheets of material and an increase in the number of fibers that form the porous structure (FIG. 18E).

TABLE 21

| Material | Mass EDC (g) | Mass NHS (g) | Reaction Time (h) |
|---|---|---|---|
| Control | 1.74 | 0.42 | 2, 4, or 16 |
| ½ Control Concentration | 0.87 | 0.42 | 4 |
| 2 Times Control Concnetration | 3.65 | 0.42 | 4 |

The ability of the crosslinked collagen material to absorb blood was also monitored. The results are shown in Table 20. By either decreasing the concentration of EDC and NHS or decreasing the reaction time, which allows fewer crosslinks to be formed, the ability of the crosslinked material to absorb blood can be decreased. This affords the ability to control absorption of blood, and to a certain extent swelling is also controlled by controlling the reaction parameters. Thus the material properties can be tailored to provide the most desirable hemostatic or wound healing device.

TABLE 20

Percent of Blood Absorbed by EDC/NHS Crosslinked Collagen.

| Material | % Blood Absorption |
| --- | --- |
| Control | 96.14 |
| ½ x | 47.25 |
| 2 x | 84.58 |
| 2 h rxn | 70.62 |
| 16 h rxn | 61.96 |

The EDC/NHS crosslinked material has an increased capacity to absorb blood compared to GTA crosslinked collagen. This is potentially because EDC/NHS attaches two or more collagen chains during crosslinking and does not alter the overall chemical composition of the collagen. GTA crosslinking, however, inserts a linker that can disrupt the spacing and interactions between collagen chains as well as alter the charge of the collagen thereby decreasing the amount of blood that can be absorbed.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and similar variations.

The disclosures of each and every patent, patent application, and publication cited herein are hereby incorporated herein by reference in their entirety.

The invention claimed is:

1. A hemostatic composition consisting essentially of crosslinked collagen scaffold reconstituted in a physiologically acceptable liquid vehicle,
   wherein the composition does not contain thrombin;
   wherein the composition is flowable and has no residual amount of a crosslinker;
   wherein concentration of the crosslinked collagen is from 50-250 mg/mL;
   wherein the crosslinked collagen scaffold, prior to reconstitution, has a porosity greater than 50% and a surface area of between 0.5 to 30 $m^2/g$; and
   wherein the composition has a percent swelling of between 0% to 20% within 10 minutes.

2. The hemostatic composition of claim 1, wherein the crosslinked collagen scaffold includes at least one material structure from the group consisting of fibers, ribbons, ropes and sheets.

3. The hemostatic composition of claim 2, wherein the number of structures is controlled by the ratio of percent collagen solids to percent crosslinker when crosslinking the collagen.

4. The hemostatic composition of claim 2, wherein the number of structures is controlled by the collagen concentration prior to freezing the collagen.

5. The hemostatic composition of claim 2, wherein the number of structures is controlled by the temperature and rate of freezing when the collagen is lyophilized.

6. The hemostatic composition of claim 1, wherein the collagen is microfibrillar collagen.

7. The hemostatic composition of claim 1, wherein the collagen is fibrillar collagen.

8. The hemostatic composition of claim 1, wherein the liquid vehicle is water, saline, calcium chloride or a combination thereof.

9. The hemostatic composition of claim 8, wherein the composition can be dispensed from a syringe having at least a 1.6 mm opening.

10. The hemostatic composition of claim 1, wherein the composition has a porosity controlled by the temperature and rate of freezing used to manufacture the composition.

11. The hemostatic composition of claim 9, wherein the flowability is controlled by the presence of at least one material structure from the group consisting of fibers, ribbons, ropes and sheets.

12. A method of promoting hemostasis at a bleeding site comprising applying the hemostatic composition of claim 1 to the bleeding site.

13. The hemostatic composition of claim 1, wherein the concentration of the crosslinked collagen is from 100-200 mg/mL.

14. A hemostatic composition consisting essentially of crosslinked collagen scaffold and thrombin reconstituted in a physiologically acceptable liquid vehicle,
   wherein the composition is flowable and has no residual amount of a crosslinker;
   wherein concentration of the crosslinked collagen is from 50-250 mg/mL;
   wherein the crosslinked collagen scaffold, prior to reconstitution, has a porosity greater than 50% and a surface area of between 0.5 to 30 $m^2/g$;
   and wherein the composition has a percent swelling of between 0% to 20% within 10 minutes.

15. The hemostatic composition of claim 14, wherein the concentration of the crosslinked collagen is from 100-200 mg/mL.

16. The hemostatic composition of claim 14, wherein the crosslinked collagen scaffold includes at least one material structure from the group consisting of fibers, ribbons, ropes and sheets.

17. The hemostatic composition of claim 14, wherein the collagen is microfibrillar collagen.

18. The hemostatic composition of claim 14, wherein the collagen is fibrillar collagen.

19. The hemostatic composition of claim 14, wherein the liquid vehicle is water, saline, calcium chloride or a combination thereof.

20. The hemostatic composition of claim 14, wherein the composition can be dispensed from a syringe having at least a 1.6 mm opening.

* * * * *